(12) United States Patent
Hammons et al.

(10) Patent No.: US 8,058,501 B2
(45) Date of Patent: *Nov. 15, 2011

(54) REGIONALIZED TOPSHEET

(75) Inventors: John Lee Hammons, Hamilton, OH (US); Sybille Fuchs, Frankfurt (DE); Luisa Valerio Gonzalez, Oakley, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 469 days.

This patent is subject to a terminal disclaimer.

(21) Appl. No.: 12/188,598

(22) Filed: Aug. 8, 2008

(65) Prior Publication Data

US 2010/0036346 A1    Feb. 11, 2010

(51) Int. Cl.
*A61F 13/15* (2006.01)
*A61F 13/20* (2006.01)

(52) U.S. Cl. ........ 604/378; 604/379; 604/383; 604/384; 604/385.01

(58) Field of Classification Search .................. 604/378, 604/379, 385.01, 383, 384
See application file for complete search history.

(56) References Cited

U.S. PATENT DOCUMENTS

| | | | |
|---|---|---|---|
| 5,180,620 A | 1/1993 | Mende | |
| 5,533,991 A | 7/1996 | Kirby | |
| 5,743,776 A | 4/1998 | Igaue et al. | |
| 5,792,404 A | 8/1998 | Cree | |
| 5,795,921 A | 8/1998 | Dyer et al. | |
| 5,849,805 A | 12/1998 | Dyer | |
| 5,873,869 A | 2/1999 | Hammons et al. | |
| 5,899,893 A | 5/1999 | Dyer et al. | |
| 5,989,478 A | 11/1999 | Ouellette et al. | |
| 6,025,049 A | 2/2000 | Ouellette et al. | |
| 6,117,523 A | 9/2000 | Sugahara | |
| 6,180,052 B1 | 1/2001 | Ouellette et al. | |
| 6,231,948 B1 | 5/2001 | Ouellette et al. | |
| 6,383,431 B1 | 5/2002 | Dobrin | |
| 6,911,574 B1 | 6/2005 | Mizutani | |
| 7,172,801 B2 | 2/2007 | Hoying et al. | |
| 7,410,683 B2 | 8/2008 | Curro et al. | |
| 7,429,689 B2 * | 9/2008 | Chen et al. | 604/378 |
| 7,507,459 B2 | 3/2009 | Turner et al. | |
| 7,553,532 B2 | 6/2009 | Turner et al. | |
| 2003/0125687 A1 | 7/2003 | Gubernick | |
| 2003/0171730 A1 * | 9/2003 | Kelly et al. | 604/383 |
| 2004/0127875 A1 | 7/2004 | Hammons et al. | |

(Continued)

FOREIGN PATENT DOCUMENTS

FR    2 713 083    6/1995

(Continued)

OTHER PUBLICATIONS

PCT International Search Report dated Aug. 10, 2009.

(Continued)

*Primary Examiner* — Tatyana Zalukaeva
*Assistant Examiner* — Ginger T Chapman
(74) *Attorney, Agent, or Firm* — Andrew J. Hagerty; Gary J. Foose

(57) ABSTRACT

An absorbent article having a liquid pervious topsheet having a first portion and a second portion. The first portion differs in structure from the second portion. The topsheet has a longitudinal centerline and a transverse centerline. The second portion has a first structurally modified zone, a second structurally modified zone, a third structurally modified zone, and a fourth structurally modified zone.

20 Claims, 20 Drawing Sheets

U.S. PATENT DOCUMENTS

| | | |
|---|---|---|
| 2004/0229008 A1 | 11/2004 | Hoying |
| 2005/0124951 A1 | 6/2005 | Kudo et al. |
| 2005/0228353 A1* | 10/2005 | Thomas .................. 604/385.01 |
| 2005/0281976 A1 | 12/2005 | Curro et al. |
| 2006/0087053 A1* | 4/2006 | O'Donnell et al. ........... 264/156 |
| 2006/0184150 A1 | 8/2006 | Noel |
| 2006/0286343 A1 | 12/2006 | Curro et al. |
| 2007/0116926 A1 | 5/2007 | Hoying |
| 2008/0119807 A1 | 5/2008 | Curro et al. |
| 2008/0154226 A9 | 6/2008 | Hammons |
| 2009/0030390 A1 | 1/2009 | Hammons |
| 2009/0030391 A1 | 1/2009 | Hammons |
| 2009/0157021 A1* | 6/2009 | Sullivan et al. ............... 604/359 |
| 2009/0157030 A1 | 6/2009 | Turner et al. |
| 2009/0209930 A1 | 8/2009 | Hammons et al. |

FOREIGN PATENT DOCUMENTS

| | | |
|---|---|---|
| WO | WO 2007/069964 | 6/2007 |
| WO | WO 2008/002219 | 1/2008 |

OTHER PUBLICATIONS

U.S. Appl. No. 12/188,492, filed Aug. 8, 2008, Hammons et al.

U.S. Appl. No. 12/188,527, filed Aug. 8, 2008, Hammons et al.

U.S. Appl. No. 12/188,543, filed Aug. 8, 2008, Hammons et al.

U.S. Appl. No. 12/470,945, filed May 22, 2009, Turner et al.

* cited by examiner

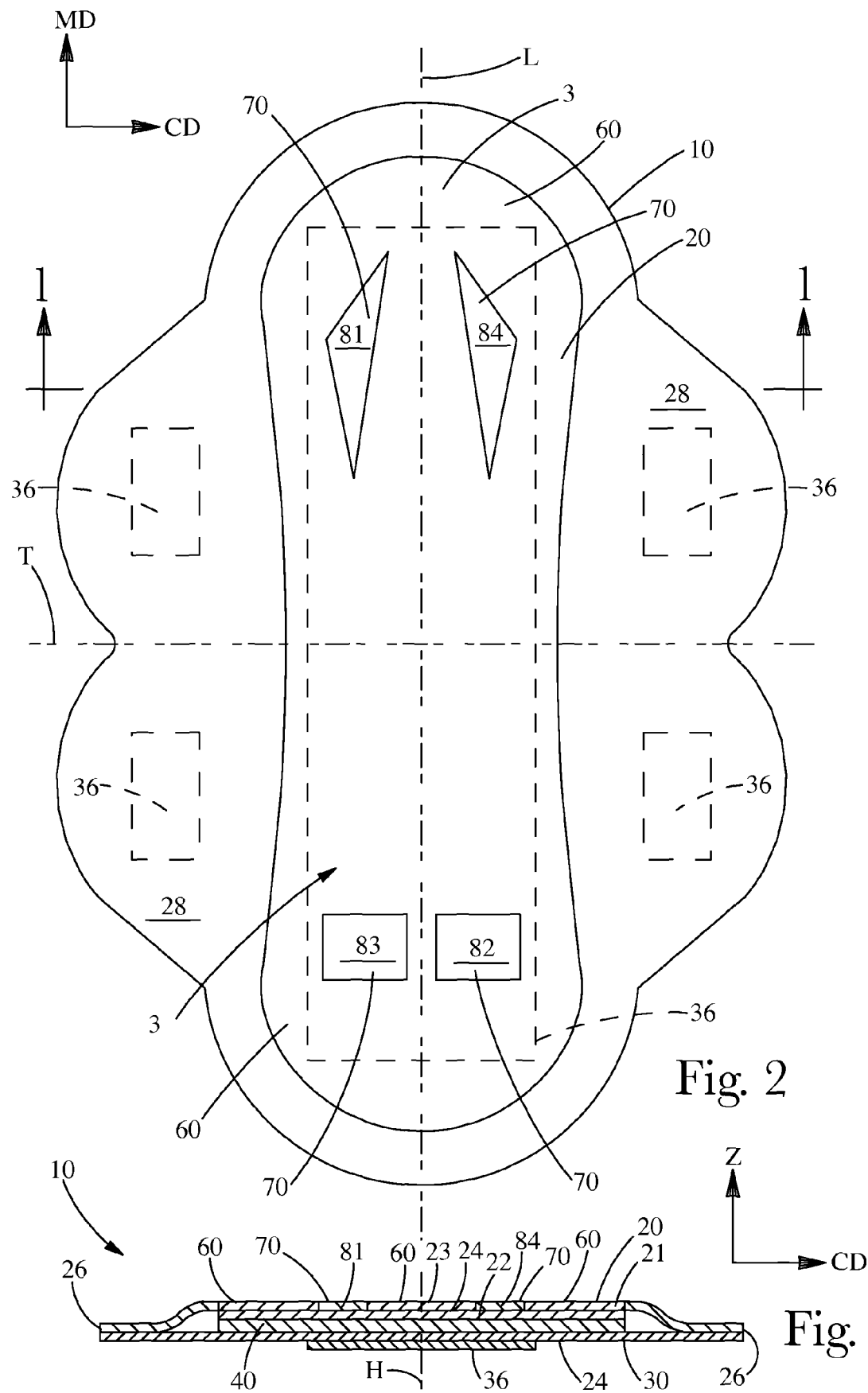

REGIONALIZED TOPSHEET

FIELD OF THE INVENTION

The present invention relates to a topsheet for an absorbent article.

BACKGROUND OF THE INVENTION

Absorbent articles such as sanitary napkins, diapers, adult incontinence products, and the like are designed to be worn in close proximity to the crotch of the wearer. The crotch region of the human body is sensitive to the physical and chemical environment around the crotch.

A woman's crotch region can comprise many different types of tissues spaced apart from one another. For instance, a woman's pubic area can be covered with pubic hair on the medial portion and adjacent to the medial portions can be soft and smooth skin. The labia majora are generally aligned along the centerline of a woman's crotch. The skin adjacent the labia majora can be soft and smooth and may have emerging hair. The anus is surrounded by soft skin. Skin further away from the anus can differ in texture from skin immediately surrounding the anus. The surface of the skin in the anal region can be different from the surface of the skin in the pubic region.

Sanitary napkins commonly cover the labia, portions of the crotch forward of the labia, portions of the crotch rearward of the labia, and portions of the crotch laterally adjacent the labia. As a woman wearing a sanitary napkin moves, portions of the sanitary napkin can rub against nearby body surfaces. Given the complex geometry of a woman's crotch region and the dynamic geometry of a woman's crotch as she moves, different portions of the woman's crotch are exposed to different rubbing forces and the friction between the sanitary napkin and wearer's crotch can vary depending on the location.

The moisture and chemical environments of a woman's crotch can also vary as a function of location. For instance, the labia majora may be exposed to menses and/or urine. The medial portion of the woman's pubic area may be exposed to perspiration. Portions adjacent the medial area may be subjected to more moisture due to the lack of hair and the tendency for a woman's panty to closely conform to the juncture of the inner thigh and the crotch and pubic area. The area near the anus may be exposed to more perspiration and anal leakage than areas further away from the anus. Absorbent articles having regionalized fluid acquisition properties that are coordinated with the moisture environment of different regions of the crotch may be beneficial for providing improved health of the skin. Similar to a woman's crotch, the crotch region of male and female infants, adult males, and females beyond the age of menstruation can also have a wide variety of physical and chemical conditions in different locations of the crotch region.

Designers of absorbent articles are faced with the challenge of designing articles that provide for healthy skin in all regions of the wearer's crotch. In some instances, the benefit of providing for skin health in one region is obtained at the expense of decreased skin health in another region. Designs that apply a uniform approach across the entire absorbent article may not provide for satisfactory skin health and fluid acquisition throughout the entire crotch region. Furthermore, skin health and the feeling of wetness can impact how comfortable the absorbent article is to wear.

With these limitations in mind, there is a need for absorbent articles having a topsheet that provides different features that provide different skin health benefits to different portions of the wearer's crotch.

SUMMARY OF THE INVENTION

An absorbent article comprising a liquid pervious topsheet comprising a first portion and a second portion. The first portion differs in structure from the second portion. The topsheet has a longitudinal centerline and a transverse centerline. The second portion comprises a first structurally modified zone and a second structurally modified zone. The first structurally modified zone and the second structurally modified zone are on opposing sides of the longitudinal centerline and the first structurally modified zone and the second structurally modified zone are on opposing sides of an axis parallel to the transverse centerline. The first structurally modified zone and the second structurally modified zone are spaced apart from one another. The first structurally modified zone and the second structurally modified zone together make up more than about 10% of the area of the topsheet.

The topsheet can further comprise a third structurally modified zone, and a fourth structurally modified zone. The third structurally modified zone can be disposed on the same side of said longitudinal centerline as the first structurally modified zone. The first structurally modified zone and the third structurally modified zone can be disposed on opposing sides of an axis parallel to said transverse centerline. The fourth structurally modified zone can be disposed on the same side of said longitudinal centerline as the second structurally modified zone and the second structurally modified zone and the fourth structurally modified zone can be disposed on opposing sides of an axis parallel to the transverse centerline. The first structurally modified zone, second structurally modified zone, third structurally modified zone, and fourth structurally modified zone can be spaced apart from one another. The first structurally modified zone, second structurally modified zone, third structurally modified zone, and fourth structurally modified zone together can comprise more than about 10% of the area of the topsheet.

BRIEF DESCRIPTION OF THE DRAWINGS

FIG. 1 is a cross section of an absorbent article as indicated by Section 1-1 in FIG. 2.

FIG. 2 is a plan view of the body-facing surface of an absorbent article having a first portion and a second portion.

DETAILED DESCRIPTION OF THE INVENTION

Figure 3:
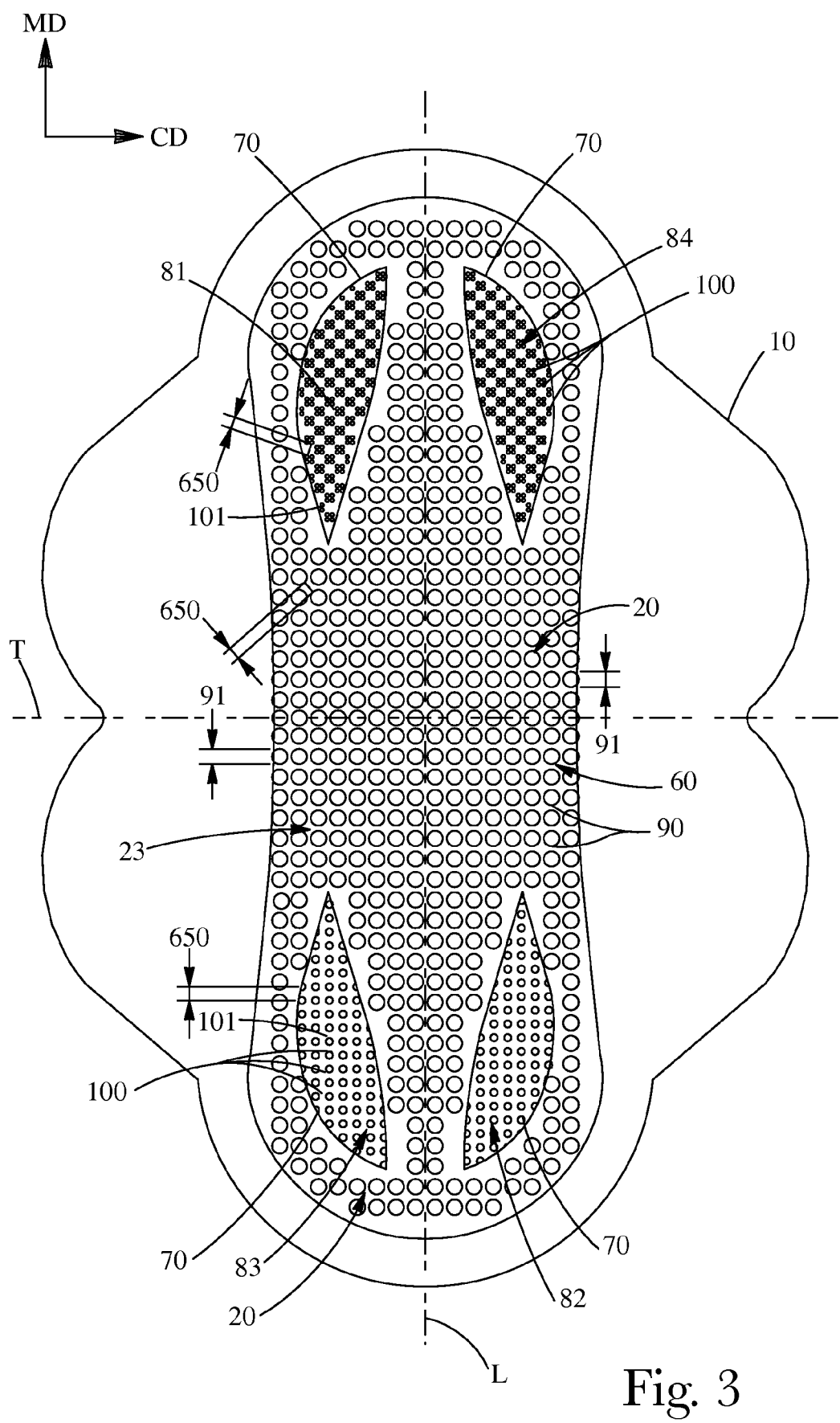
FIG. 3 is a plan view of the body-facing surface of an absorbent article having a first portion and a second portion.

As used herein, "structurally modified", with respect to constituent materials, means that the constituent material (or materials) is altered such that a material that is structurally modified differs in mechanical behavior as compared to the unmodified material. For instance, the structurally modified material can transmit stress (or deform) differently than the unmodified material. The structure of the material can be altered on a molecular level and/or by disrupting the continuity and/or physical arrangement of portions of the material. "Structure" refers to the physical arrangement of the constituent material that governs mechanical behavior (e.g. how stress is transmitted through the material).

As used herein, a structurally modified zone is not a channel. As used herein, a "channel" is an indentation having an in-plane length greater than the width, the length being the longest dimension, curved or straight, within the indentation and the in-plane width being the shortest dimension of the indentation. As used herein, a structurally modified zone does not comprise indentations, dimples, or embossments, i.e., structure created by compressing portions of the absorbent article. A structurally modified zone includes, but is not limited to, apertures and tufts.

As used herein, the word "zone" refers to an area set off as distinct from surrounding or adjoining areas. Thus, for example, a topsheet comprising uniformly spaced apertures, each of which are the same size, over the entire surface of the topsheet cannot be considered to have any zones of apertures. Moreover, for example, in a topsheet comprising uniformly spaced apertures, each of which are the same size, a single aperture and locally surrounding material cannot be considered a zone of apertures because that single aperture and locally surrounding material are not distinct from surrounding or adjoining areas. Similarly, for example, a topsheet comprising uniformly spaced elements, each element being the same, over the entire surface of the topsheet cannot be considered to have any zones of elements. Nor, in a topsheet comprising uniformly spaced elements, for example, may a single element and locally surrounding material be considered a zone. Zones can be separated from one another such that there is an absence of like structured material between the zones (i.e. the first structurally modified zone, the second structurally modified zone, the third structurally modified zone, and the fourth structurally modified zone).

As used herein, "elements" are discrete portions of the constituent material that are structurally disrupted. Examples of an element include, but are not limited to, an aperture and a tuft. An indentation, dimple, or embossment, i.e., structure created by compressing portions of the absorbent article, is not an element.

As used herein, two elements are "integral" with one another provided that the elements are formed from the same precursor material or precursor materials. A lotion applied to a topsheet is not integral with the topsheet, as the lotion and topsheet are not formed from the same precursor materials.

As used herein, a "difference in color" refers to a difference or visual distinction in color as characterized by the CIE LAB scale. Differences in color can be measured using a Hunter Color reflectance meter available from Hunter Associates Laboratory, Inc., Reston, Va.

As used herein, "area density" refers to the number of features per unit area. The features can be macrofeatures or microfeatures, as described herein.

As used herein, two objects are "engaged" with one another when stress can be transmitted from one object to the other object.

As used herein, the term "nonwoven web" refers to a web having a structure of individual fibers or threads which are interlaid, but not in a repeating pattern as in a woven or knitted fabric, which do not have randomly oriented fibers. Nonwoven webs or fabrics can be formed from many known processes, such as, for example, air laying processes, melt-blowing processes, spunbonding processes, hydroentangling processes, spunlacing processes, and bonded carded web processes. Also, multi-layer webs, such as spunbond-meltblown-spunbond webs and the like made by multiple beam spunbond processes, can be used.

As used herein, the term "polymer" is used in its conventional meaning, and generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries. In general, any of the known polymer types can be used, for example, polyolefinic polymers such as polypropylene or polyethylene can be used either as monocomponent fibers or bicomponent fibers. Other polymers such as PVA, PET polyesters, metallocene catalyst elastomers, nylon and blends thereof can be used. Any or all of the polymers can be cross-linked if desired.

FIG. 1 is an illustration of a cross section of an embodiment of an absorbent article 10 providing for different skin health benefits and fluid acquisition benefits for different portions of the wearer's crotch. The absorbent article 10 can comprise a liquid pervious topsheet 20, a fluid impervious backsheet 30, and an absorbent core 40 disposed between the topsheet 20 and backsheet 30. The topsheet 20 can be a composite topsheet 20 comprised of an upper layer 21 and a lower layer 22 that are engaged with one another in a layered relationship. The topsheet 20 can be described as being in a facing relationship with absorbent core 40.

The absorbent article 10 is discussed herein in the context of what is commonly referred to in the art as a sanitary napkin, menstrual pad, or catamenial pad. It is to be understood that the absorbent article 10 can also be any absorbent article designed to be worn in proximity with the crotch of the wearer. The absorbent article can be a consumer product selected from the group consisting of a sanitary napkin, an adult incontinence product, and a diaper.

The absorbent article 10 and each layer or component thereof can be described as having a body facing surface and a garment facing surface. As can be understood by considering the ultimate use for absorbent articles, such as sanitary napkins, diapers, incontinent products and the like, the body facing surfaces are the surfaces of the layers or components that are oriented closer to the body when in use, and the garment facing surfaces are the surfaces that are oriented closer to the undergarment of the wearer when in use. Therefore, for example, the topsheet 20 has a body facing surface 23 (that can actually be a body contacting surface) and a garment facing surface 24 that can be adhered to an underlying secondary topsheet. The garment facing surface 24 of the backsheet 30, for example, can be oriented closest to, and can contact the wearer's panties in use (via a positioning adhesive 36 if used).

The absorbent article 10 has an absorbent article width measured between the lateral edges 26 measured in the cross direction CD. The absorbent article 10 has a vertical axis H. The absorbent article 10 has a thickness measured in the z-direction.

The topsheet 20 is comprised of a first portion 60 and a second portion 70, wherein the first portion 60 differs in structure from the second portion 70. The second portion 70 can comprise a first structurally modified zone 81. The second portion 70 can comprise a fourth structurally modified zone 84. The first portion 60 and second portion 70 can be comprised of a continuous web of material. The first portion 60 and the second portion 70 can be comprised of the same precursor material or materials. A continuous web of material can be comprised of a single unitary web.

As shown in FIG. 2, the topsheet 20 can have a longitudinal centerline L and a transverse centerline T. Longitudinal centerline L and transverse centerline T define a two-dimensional plane of the topsheet 20 prior to use, which, in the embodiment shown, is associated with the machine direction (MD) and cross machine direction (CD) as is commonly known in the art of making articles using production lines. The absorbent article 10 has a length, which is the longest dimension measured parallel to the longitudinal centerline L. The absorbent article has a width, which is the dimension measured in the CD, e.g., parallel to the transverse centerline T. The transverse centerline T intersects the longitudinal centerline L at mid-length of the longitudinal centerline L. The width of the absorbent article 10 can vary or be substantially constant along the length of the absorbent article 10. For descriptive purposes, the absorbent article 10 has a longitudinal centerline and transverse centerline taken to be coincident with the longitudinal centerline L and transverse centerline T, respectively. The actual longitudinal centerline and the transverse centerline of the absorbent article 10 need not be coincident with the longitudinal centerline L and transverse centerline T of the topsheet 20. The topsheet 20 has a vertical axis that can be taken to be coincident with the vertical axis H of the absorbent article 10. The area 3 of the topsheet 20 is in the MD-CD plane.

Absorbent article 10 can have wings 28, also known as side extensions or flaps, designed to wrap the sides of the crotch region of the panties and attach thereto. Absorbent article 10 and/or wings 28 can have fastening means including attachment components, such as pressure sensitive positioning adhesive 36. The absorbent article 10 can have strips of positioning adhesive 36 on the garment facing surface 24 of the backsheet 30. The positioning adhesive can be hot-melt adhesive material capable of establishing a temporary bond with the undergarment material such as HL-1491 XZP commercially available from H. B. Fuller, Toronto, Ontario, Canada.

The second portion 70 can comprise a first structurally modified zone 81 and a second structurally modified zone 82. The first structurally modified zone 81 and second structurally modified zone 82 can be on opposing sides of the longitudinal centerline L. The first structurally modified zone 81 and the second structurally modified zone 82 can be on opposing sides of an axis parallel to the transverse centerline T. That is, the first structurally modified zone 81 and the second structurally modified zone can be located in diagonally opposing quadrants of the topsheet 20, the quadrants being demarcated by the longitudinal centerline L and an axis parallel to the transverse centerline T. The first structurally modified zone 81 and the second structurally modified zone 82 can be spaced apart from one another.

The second portion 70 can comprise a third structurally modified zone 83 that is disposed on the same side of the longitudinal centerline L as the first structurally modified zone 81, wherein the first structurally modified zone 81 and the third structurally modified zone 83 are disposed on opposing sides of an axis parallel to the transverse centerline T. The first structurally modified zone 81, second structurally modified zone 82, and third structurally modified zone 83 can be spaced apart from one another.

The second portion 70 can comprise a fourth structurally modified zone 84 that is disposed on the same side of the longitudinal centerline L as the second structurally modified zone 82, wherein the second structurally modified zone 82 and the fourth structurally modified zone 84 are disposed on opposing sides of an axis parallel to the transverse centerline T. The first structurally modified zone 81, second structurally modified zone 82, third structurally modified zone 83, and fourth structurally modified zone 84 can be spaced apart from one another.

In an embodiment in which the second portion comprises a first structurally modified zone 81, a second structurally modified zone 82, a third structurally modified zone 83, and a fourth structurally modified zone 84, the structurally modified zones can be spaced apart from one another such that each of the structurally modified zones is individually located in a quadrant of the topsheet 20.

The first portion 60 can comprise the part of the topsheet 20 having a physical structure that differs from the first structurally modified zone 81 and the second structurally modified zone 82. The first portion 60 can comprise the part of the topsheet 20 having a physical structure that differs from the first structurally modified zone 81, the second structurally modified zone 82, the third structurally modified zone 83, and fourth structurally modified zone 84. The second portion 70 can comprise the first structurally modified zone 81 and the second structurally modified zone 82. The second portion 70 can comprise the first structurally modified zone 81, the second structurally modified zone 82, the third structurally modified zone 83, and fourth structurally modified zone 84. That is, the second portion 70 can be that part of the topsheet 20 that is not the first portion 60.

As used herein, one or more of the first structurally modified zone 81, second structurally modified zone 82, third structurally modified zone 83, and fourth structurally modified zone 84 are referred to generically as the structurally modified zone(s). The structurally modified zones can be integral with the topsheet 20. That is, the topsheet 20 is comprised of two or more of the first structurally modified zone 81, second structurally modified zone 82, third structurally modified zone 83, and fourth structurally modified zone 84. The structurally modified zones and first portion 60 can be comprised of a continuous web or webs of material. Each of the structurally modified zones can be comprised of the same precursor materials. The structurally modified zones and the first portion 60 can be comprised of two or more layers engaged with one another in a layered relationship, for example, as in a laminate.

As shown in FIG. 3, the structurally modified zones need not all be the same. For instance, the structures (such as second apertures 100 or other structural features contemplated herein) defining the structurally modified zones can have different sizes and/or be arranged in a different pattern to deliver different performance benefits, such as comfort, to different portions of the body.

In one embodiment, the first structurally modified zone 81, second structurally modified zone 82, third structurally modified zone 83, and fourth structurally modified zone 84 can be separated from one another by at least the maximum dimension (in the plane defined by the longitudinal centerline L and transverse centerline T) of the largest of the structurally modified zones.

By spacing apart the first structurally modified zone 81 and the second structurally modified zone 82, it is thought that different benefits to skin health and fluid acquisition can be targeted to different portions of the wearer's body. If a third structurally modified zone 83 and/or fourth structurally modified zone 84 is present, it is thought that a similar benefit can be obtained by spacing apart the structurally modified zones. For instance, the body facing surface 23 of the topsheet 20 proximal the wearer's anus can have a different texture than the body facing surface 23 of the topsheet 20 proximal to portions of the wearer's body away from the anus. Similarly, the body facing surface 23 of the topsheet 20 proximal the wearer's labia majora can have a different texture than the body facing surface 23 of the topsheet 20 proximal the junction between the wearer's thigh and pubic area. Skin health may also depend on the moisture conditions in and on different regions of the absorbent article associated with wearing the absorbent article. Thus, fluid acquisition and retention of the absorbent article may affect health of the skin. Furthermore, by spacing apart the first structurally modified zone 81, second structurally modified zone 82, third structurally modified zone 83, and fourth structurally modified zone 84, it may be possible to provide for improved fluid handling in the central part of the topsheet while maintaining adequate barrier functions along the lateral sides of the topsheet 20 and the front and rear of the topsheet 20. An additional benefit that may arise is that the first structurally modified zone 81, second structurally modified zone 82, third structurally modified zone 83, and fourth structurally modified zone 84 can be laid out to provide for enhanced comfort about portions of the periphery of the topsheet 20.

The structurally modified zones can comprise more than about 2% of the topsheet area, the area being measured in the plane of the longitudinal centerline L and transverse centerline T of the topsheet 20. The structurally modified zones can comprise more than about 5% of the topsheet area. The structurally modified zones can comprise more than about 10% of the topsheet area. The structurally modified zones can comprise more than about 20% of the topsheet area. The structurally modified zones can comprise more than about 40% of the topsheet area. The structurally modified zones can comprise more than about 60% of the topsheet area.

The first structurally modified zone 81, second structurally modified zone 82, third structurally modified zone 83, and fourth structurally modified zone 84 can have a unique structure as compared to one or more other structurally modified zones. The structurally modified zones can each have the same structure.

The structurally modified zones can comprise macro features. Macro features are elements that are visible to the unaided eye of a person having 20/20 vision from a distance of 30 cm in lighting at least equal to the illumination of a standard 100 watt incandescent white light bulb. Macro features can be elements having an area in the MD-CD plane greater than about 0.25 mm$^2$. Macro features can be elements having an area in the MD-CD plane greater than about 1 mm$^2$. Macro features can be elements having an area in the MD-CD plane greater than about 2 mm$^2$. Macro features can be elements having an area in the MD-CD plane less than about 5 mm$^2$. Macro features can be spaced apart from one another by about 1 mm or greater on center.

By way of example and not to be limiting, a macrofeature can be a single aperture, a single tuft, or a single aperture protruding out of the MD-CD plane. Macrofeatures other than tufts, apertures, and apertures protruding out of the MD-CD plane are contemplated. The structurally modified zones can be defined by a plurality of spaced apart macro features, wherein the structurally modified zones are spaced apart from one another by a distance greater than the maximum spacing 650 between adjacent macro features, as shown in FIG. 3.

The structurally modified zones can comprise micro features. Micro features are elements that are not visible to the unaided eye of a person having 20/20 vision from a distance of 30 cm in lighting at least equal to the illumination of a standard 100 watt incandescent white light bulb. The structurally modified zones can be defined by a plurality of spaced apart micro features, wherein the structurally modified zones are spaced apart from one another by a distance greater than the maximum spacing 650 between adjacent micro features. Micro features are smaller than macro features.

By way of example and not to be limiting, a microfeature can be a single aperture, a single tuft, or a single aperture protruding out of the MD-CD plane. Microfeatures other than tufts, apertures, and apertures protruding out of the MD-CD plane are contemplated. By way of example, and not to be limiting, the structurally modified zones can comprise apertures or tufts. Structurally modified zones can comprise other elements or structures that provide for skin health and/or improved fluid acquisition.

The first portion 60 can have first apertures 90 and the second portion 70 can have second apertures 100, as shown in FIG. 3. The second apertures 100 can differ, for example differ in structure, from the first apertures 90. For instance, first apertures 90 and second apertures 100 can be circular opening, the difference being that first apertures 90 and second apertures 100 have a different diameter. Without being bound by theory, it is thought that materials or structurally modified zones having different apertures can interact differently with the wearer's skin. For instance, a topsheet 20 having small apertures may feel softer and be less abrasive to the wearer's skin than a topsheet 20 having large apertures. Similarly, it is thought that materials having one size and shape of apertures may acquire and retain fluid and/or moisture in a manner that differs from materials having another size and/or shape of apertures, which may ultimately provide improved skin health to the wearer. Individual first apertures 90 and second apertures 100 can have an area between about 0.1 mm and about 4 mm and any area there between in about 0.1 mm$^2$ increments. Individual first apertures 90 and second apertures 100 can have an area of about 0.25 mm$^2$, about 1 mm$^2$, or about 2 mm$^2$. Individual first apertures 90 and second apertures 100 can have an area greater than about 0.25 mm$^2$.

The in-plane size of individual second apertures 100 can differ from the in-plane size of individual first apertures 90, as shown in FIG. 3. The size of an aperture is the largest dimension of the aperture in the MD-CD plane (the body facing surface 23 being presented to the viewer of the topsheet). The first apertures 90 have a first size 91 defined by the largest dimension of the first apertures 90 and the second apertures 100 have a second size 101 defined by the largest dimension of the second apertures 100. The second size 101 of the second apertures 100 can differ from the first size 91 of the first apertures 90. The second size 101 of the second apertures 100 can be greater than the first size 91 of the first apertures 90. The second size of the second apertures 100 can be smaller than the first size 91 of the first apertures 90.

Figure 4:
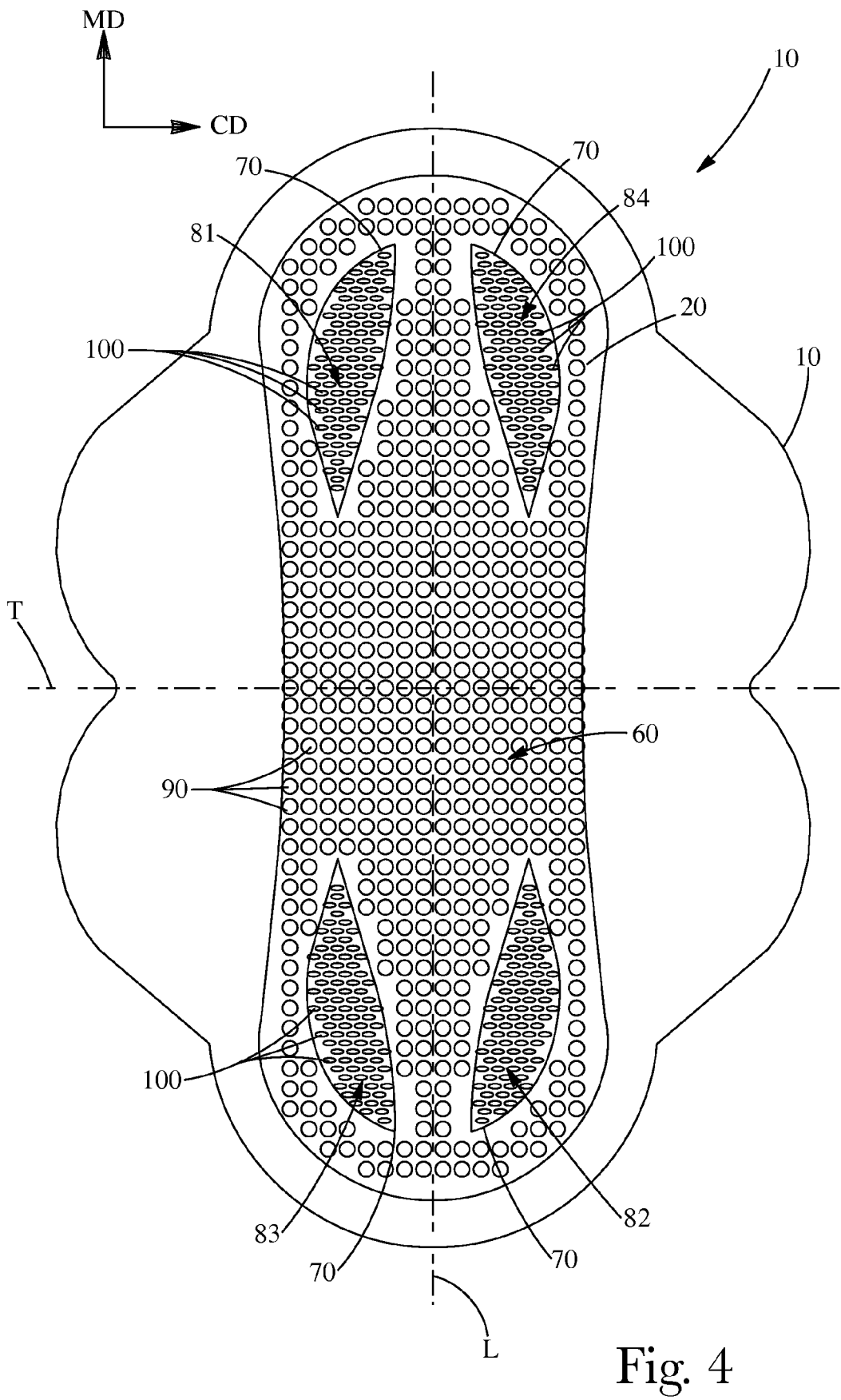
FIG. 4 is a plan view of an absorbent article having a first portion and a second portion.

The in-plane geometry of individual first apertures 90 can differ from the in-plane geometry of individual second apertures 100. In-plane geometry refers to the shape of the object as presented to a viewer looking at the body facing surface 23 of the topsheet 20 so that the MD-CD plane is facing the viewer. For instance, as shown in FIG. 4, first apertures 90 can have a substantially circular shape and the second apertures 100 can have a substantially oval shape. Without being bound by theory, it is thought that the shape of apertures in a material can affect how smooth a material is perceived to be. For instance, materials having oval shaped apertures may feel smoother than materials having circular shaped apertures when the material is stroked by a person in a direction parallel to the major axis of the oval shaped apertures even if the minor axis of the oval shaped apertures and diameter of the circular shaped apertures are about the same. Apertures having an oval shape can have a ratio of major axis dimension to minor axis dimension greater than 1. Apertures having an oval shape can have a ratio of major axis dimension to minor axis dimension greater than about 1.5.

The out of plane geometry of the first portion 60 can differ from the out-of-plane geometry of the second portion 70. The in-plane orientation of the topsheet 20 can be defined by the longitudinal centerline L and the transverse centerline T of the topsheet 20. If the first portion 60 and the second portion 70 comprise apertures, the out-of-plane geometry of individual first apertures 90 can differ from the out-of-plane geometry of individual second apertures 100. Out-of-plane geometry refers the shape presented to a viewer looking at a cross-section of the material orthogonal to the MD-CD plane, with the first portion having a first portion out-of-plane geometry and the second portion having a second portion out-of-plane geometry. Out-of-plane geometry can be sensed visually by an observer. In some instances, the out-of-plane geometry of different portions of the topsheet 20 can provide different tactile sensations. That is, the first portion 60 and second portion 70 of the topsheet 20 can feel different. In the art of garments worn in proximity to the human body, the feel of a material or fabric is referred to as "hand".

Figure 5:
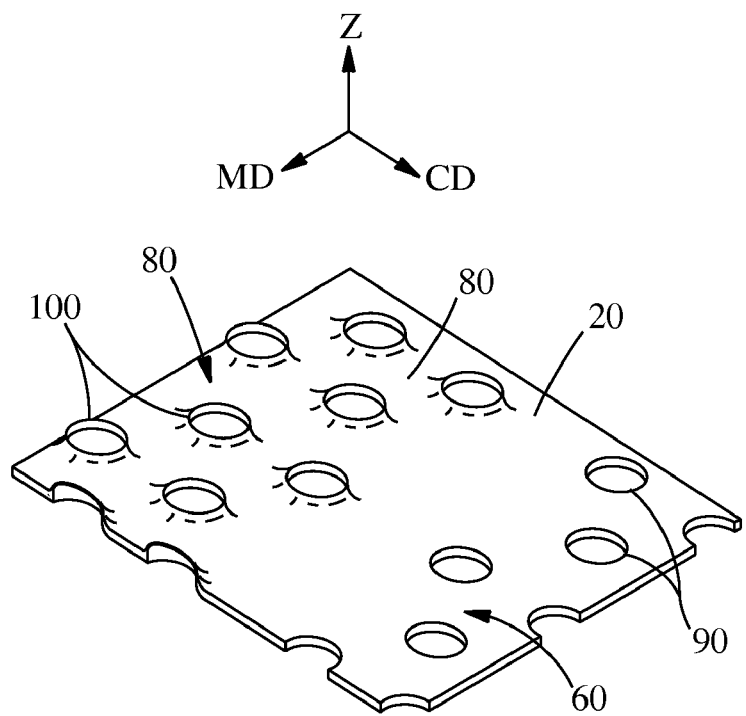
FIG. 5 is a schematic of a portion of a topsheet.

A portion of a topsheet 20 is illustrated in FIG. 5. As shown in FIG. 5, first apertures 90 in the first portion 60 can be substantially flat in the MD-CD plane. Second apertures 100 in the second portion 70 can protrude out of the MD-CD plane in the z direction. Without being bound by theory, a material having apertures protruding out of the MD-CD plane may feel smoother or rougher than a material having apertures in plane, depending on the deformability of the material and the geometry of the out-of-plane protrusion and the geometry of the rim of the aperture.

The first portion can have a first portion aperture area density and the second portion can have a second portion aperture area density. The first portion aperture area density can differ from the second portion aperture area density.

The topsheet 20 can be film, a nonwoven, or a laminate. A laminate topsheet can comprise two layers of film, two layers of nonwoven, or a layer of nonwoven with a film. Apertures can include micro apertures and macro apertures. Macro apertures are apertures that are visible to the unaided eye of a person having 20/20 vision from a distance of 30 cm in lighting at least equal to the illumination of a standard 100 watt incandescent white light bulb. Macro apertures can be elements having an area in the MD-CD plane greater than about 0.25 mm$^2$. Micro apertures are apertures that are not visible to the unaided eye of a person having 20/20 vision from a distance of 30 cm in lighting at least equal to the illumination of a standard 100 watt incandescent white light bulb. Micro apertures and/or other texturing can be formed prior to processing as described herein.

Figure 6:
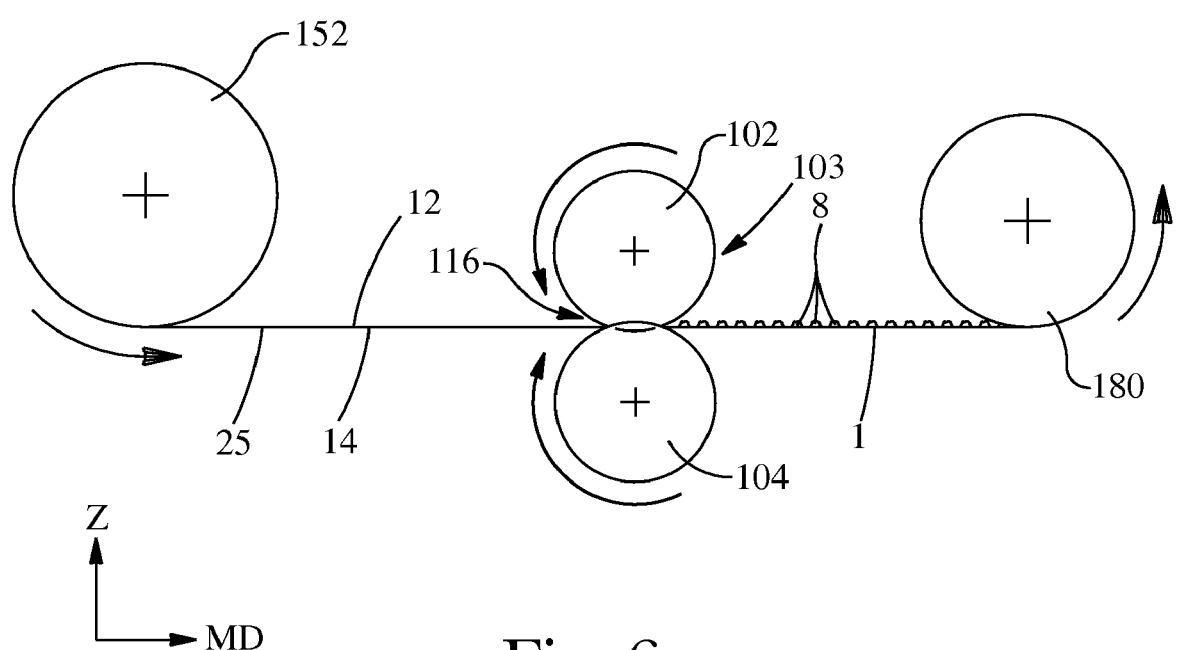
FIG. 6 is a schematic of an apparatus for forming a web having apertures.

An apertured web 1, which can be used as a topsheet 20, can be formed as shown in FIG. 6. As shown in FIG. 6, web 1 can be formed from a generally planar, two dimensional precursor web 25 having a first side 12 and a second side 14. Precursor web 25 can be, for example, a polymer film, a nonwoven web, a woven fabric, a paper web, a tissue paper web, or a knitted fabric, or a multilayer laminate of any of the aforementioned. In general, the term "side" is used herein in the common usage of the term to describe the two major surfaces of generally two-dimensional webs, such as paper and films. In a composite or laminate structure, the first side 12 of the web 1 is the first side of one of the outermost layers or plies, and the second side 14 is the second side of the other outermost layer or ply.

Precursor web 25 can be a polymeric film web. Polymeric film webs can be deformable. Deformable, as used herein, describes a material which, when stretched beyond its elastic limit, will substantially retain its newly formed conformation. Such deformable materials may be chemically homogeneous or heterogeneous, such as homopolymers and polymer blends, structurally homogeneous or heterogeneous, such as plain sheets or laminates, or any combination of such materials.

Deformable polymeric film webs that can be used can have a transformation temperature range in which changes in the solid state molecular structure of the material occur. Changes in the structure can include a change in crystalline structure and/or a change from solid to molten state. As a consequence, above the transformation temperature range, certain physical properties of the material are substantially altered. For a thermoplastic film, the transformation temperature range is the melt temperature range of the film, above which the film is in a molten state and loses substantially all previous thermo-mechanical history.

Polymeric film webs can comprise thermoplastic polymers having characteristic Theological properties which depend on their composition and temperature. Below their glass transition temperature, such thermoplastic polymers can be hard, stiff, and/or brittle. Below the glass transition temperature, the molecules are in rigid, fixed positions. Above the glass transition temperature but below the melt temperature range, thermoplastic polymers exhibit viscoelasticity. In this temperature range, the thermoplastic material generally has a certain degree of crystallinity, and is generally flexible and to some degree deformable under a force. The deformability of such a thermoplastic is dependent on the rate of deformation, amount (dimensional quantity) of deformation, length of time it is deformed, and its temperature. In one embodiment, processes can be utilized to form materials comprising thermoplastic polymers, especially thermoplastic film, which are within this viscoelastic temperature range.

Polymeric film webs can comprise a certain amount of ductility. Ductility, as used herein, is the amount of permanent, unrecoverable, plastic strain which occurs when a material is deformed, prior to failure (rupture, breakage, or separation) of the material. Materials that can be used as described herein can have a minimum ductility of at least about 10%, or at least about 50%, or at least about 100%, or at least about 200%.

Polymeric film webs can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. As noted below, polymeric film webs can be textured or otherwise altered from a strictly flat, planar configuration.

Precursor web 25 can be a nonwoven web. For nonwoven precursor webs 25, the precursor web 25 can comprise unbonded fibers, entangled fibers, tow fibers, or the like. Fibers can be extensible and/or elastic, and may be pre-stretched for processing. Fibers of precursor web 25 can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers.

Nonwoven precursor webs 25 can be any known nonwoven webs comprising polymer fibers having sufficient elongation properties to be formed into apertured web 1. In general, the polymeric fibers can be bondable, either by chemical bond (e.g. by latex or adhesive bonding), pressure bonding, or thermal bonding. If thermal bonding techniques are used in the bonding process described below, a certain percentage of thermoplastic material, such as thermoplastic powder or fibers can be used to facilitate thermal bonding of portions of fibers in the web, as discussed more fully below. Nonwoven precursor web 25 can comprise about 100% by weight thermoplastic fibers. Nonwoven precursor web 25 can comprise as little as about 10% by weight thermoplastic fibers. Likewise, nonwoven precursor web 25 can comprise any amount by weight thermoplastic fibers in 1% increments between about 10% and about 100%.

Precursor web 25 can be a composite or a laminate of two or more precursor webs, and can comprise two or more nonwoven webs or a combination of polymer films, nonwoven webs, woven fabrics, paper webs, tissue webs, or knitted fabrics. Precursor web 25 can be supplied from a supply roll 152 (or supply rolls, as needed for multiple web laminates) or any other supply means, such as festooned webs, as is known in the art. In one embodiment, precursor web 25 can be supplied directly from a web making apparatus, such as a polymer film extruder or a nonwoven web-making production line.

The total basis weight of precursor web 25 (including laminate or multi-layer precursor webs 25) can range from about 8 gsm to about 500 gsm, depending on the ultimate use of the web 1, and can be produced in 1 gsm increments between about 8 and about 500 gsm. The constituent fibers of nonwoven precursor web 25 can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis-for elliptical shaped fibers, longest straight line dimension for irregular shapes) ranging from about 0.1 to about 500 microns in 0.1 micron increments.

Precursor web 25 can be preheated by means known in the art, such as by radiant heating, forced air heating, convection heating, or by heating over oil-heated rollers. Precursor web 25 can be treated with coatings, such as with surfactants, lotions, adhesives, and the like. Treating precursor web 25 can be achieved by means known in the art such as by spraying, slot coating, extruding, or otherwise applying coatings to one or both surfaces.

Supply roll 152 rotates in the direction indicated by the arrow in FIG. 6 as precursor web 25 is moved in the machine direction by means known in the art, including over or around any of various idler rollers, tension-control rollers, and the like to the nip 116 of a pair of counter-rotating rolls 102 and 104. The rolls 102 and 104 can comprise forming apparatus 103. The pair of rolls 102 and 104 can operate to form volcano shaped structures 8 and apertures in precursor web 25. Apertured web 1 can be taken up on wind up roll 180.

There are a variety of approaches for creating apertures in webs. Factors that can influence the approach selected for creating apertures include, but are not limited to, whether the precursor web 25 is a nonwoven or polymeric film, the desired geometry of the aperture, the desired processing speed, and the amount of control of the process that is desired.

Figure 7:
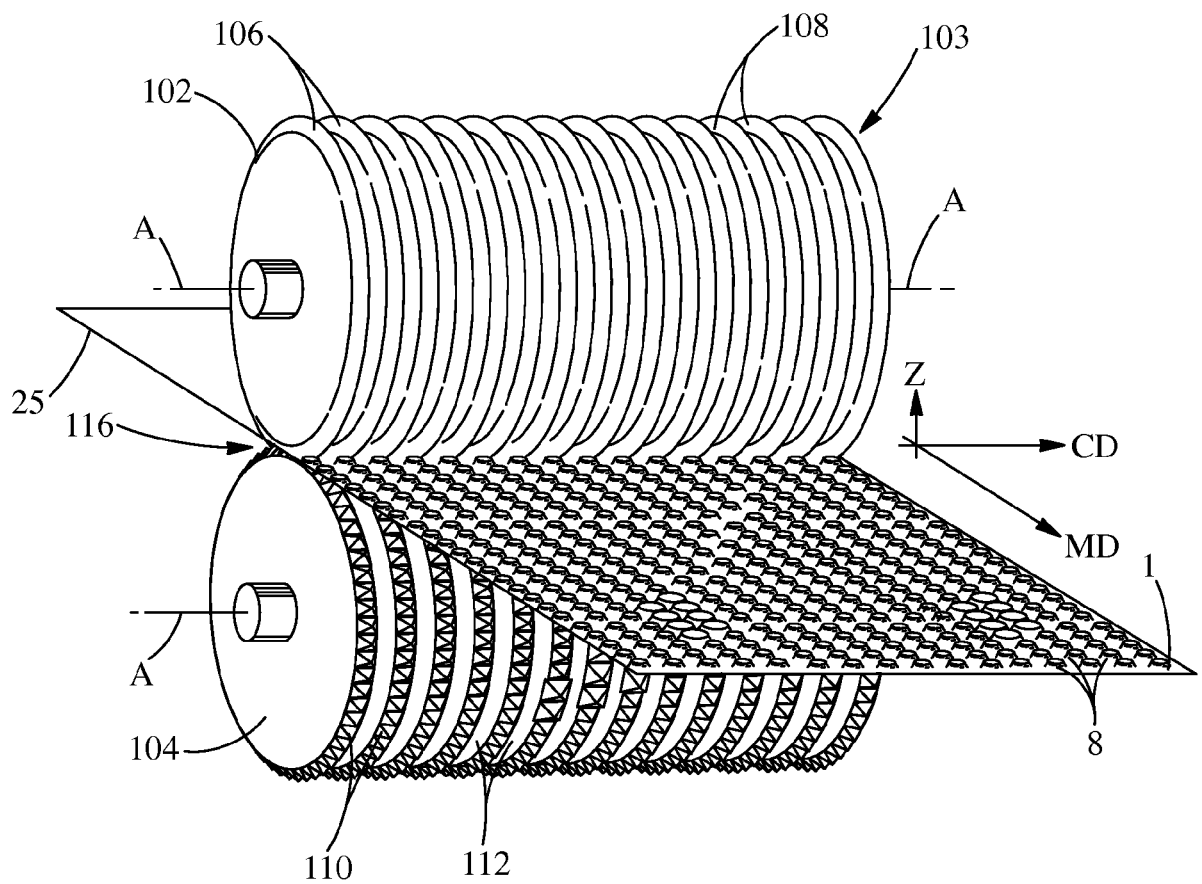
FIG. 7 is a schematic of an apparatus for forming a web having apertures.

An approach for forming apertures in polymeric film webs and nonwoven webs is to employ a pair of intermeshing rolls 102 and 104, as shown in FIG. 7 and disclosed in U.S. patent application Ser. No. 11/249,618 by O'Donnell et al. Referring to FIG. 7, there is shown in more detail the portion of the apparatus shown in FIG. 6 that can form apertured web 1. Forming apparatus 103 can comprise a pair of steel intermeshing rolls 102 and 104, each rotating about an axis A, the axes A being parallel and in the same plane. Forming apparatus 103 can be designed such that precursor web 25 remains on roll 104 through a certain angle of rotation. FIG. 7 shows in principle what happens as precursor web 25 goes straight through nip 116 on forming apparatus 103 and exits as apertured web 1. Precursor web 25 or apertured web 1 can be partially wrapped on either of rolls 102 or 104 through a predetermined angle of rotation prior to (for precursor web 25) or after (for web 1) nip 116.

Roll 102 can comprise a plurality of ridges 106 and corresponding valleys 108 which can extend unbroken about the entire circumference of roll 102. Depending on what kind of pattern is desired in apertured web 1, roll 102 can comprise ridges 106 wherein portions have been removed, such as by etching, milling or other machining processes, such that some or all of ridges 106 are not circumferentially continuous, but have breaks or gaps. Ridges 106 can be spaced apart from one another along the axis A of roll 102. For instance, the middle third of roll 102 can be smooth and the outer thirds of roll 102 can have a plurality of ridges that are spaced apart from one another. Similarly, ridges 106 on the middle third of roll 102 can be spaced more closely together than ridges 106 on the outer thirds of roll 102. The breaks or gaps, in either the circumferential direction, axial direction, or both directions, can be arranged to form a pattern, including geometric patterns such as circles or diamonds. In one embodiment, roll 102 can have teeth, similar to the teeth 110 on roll 104, described below. In this manner, it is possible to have three dimensional apertures having portions extending outwardly on both sides of apertured web 1.

Roll 104 can comprise a plurality of rows of circumferentially-extending ridges that have been modified to be rows of circumferentially-spaced teeth 110 that extend in spaced relationship about at least a portion of roll 104. The individual rows of teeth 110 of roll 104 can be separated by corresponding grooves 112. In operation, rolls 102 and 104 intermesh such that the ridges 106 of roll 102 extend into the grooves 112 of roll 104 and the teeth 110 of roll 104 extend into the valleys 108 of roll 102. Both or either of rolls 102 and 104 can be heated by means known in the art such as by incorporating hot oil filled rollers or electrically-heated rollers. Alternatively, both or either of the rolls may be heated by surface convection or by surface radiation. As shown in FIG. 7, the spacing and size of the teeth 110 can be varied. The spacing and/or size of the teeth 110 and grooves 112 on one portion of the roll 104 can be different from the spacing and/or size of the teeth 110 and grooves 112 on another portion of roll 104. This will allow different portions of an apertured web 1, which can form topsheet 20, to have first and second portions that differ from one another. Portions of roll 104 can be without teeth 110 so that portions of web 1 can be without apertures. As shown in schematic in FIG. 7, truncated generally conical shaped structures 8 can be formed in precursor web 25.

Figure 8:
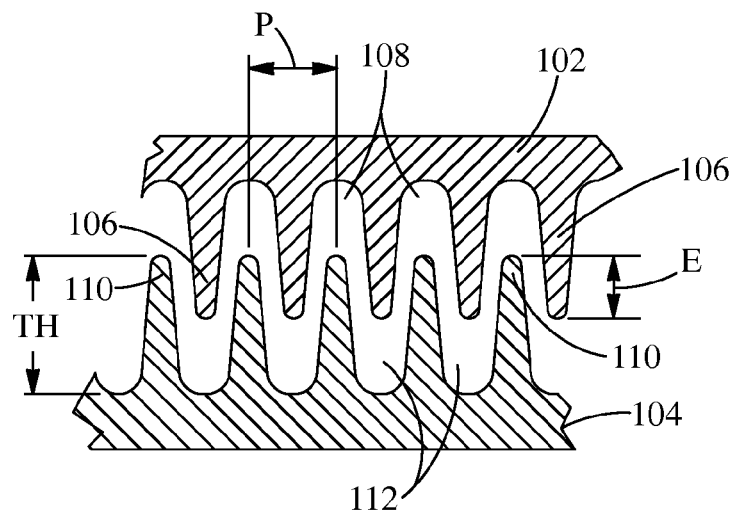
FIG. 8 is a schematic of how the teeth and grooves interengage with one another.

A schematic of a cross section of a portion of the intermeshing rolls 102 and 104 including ridges 106 and representative teeth 110 is shown in FIG. 8. As shown, teeth 110 have a tooth height TH (note that TH can also be applied to ridge 106 height and tooth height and ridge height can be equal) and a tooth-to-tooth spacing (or ridge-to-ridge spacing) referred to as the pitch P. As shown, depth of engagement, (DOE) E is a measure of the level of intermeshing of rolls 102 and 104 and is measured from tip of ridge 106 to tip of tooth 110. The depth of engagement E, tooth height TH, and pitch P can be varied as desired depending on the properties of precursor web 25 and the desired characteristics of apertured web 1.

In one embodiment, the dimensions of ridges, grooves, and/or teeth are machined to account for thermal expansion, such that the dimensions shown in FIG. 8 and dimensions described herein are dimensions at operating temperature. The rolls 102 and 104 can be made of wear resistant stainless steel.

The aperture area density can be varied from about 1 aperture/$cm^2$ to about 6 apertures/$cm^2$ to about 60 apertures/$cm^2$, in increments of 1 aperture/$cm^2$. There can be, for example, at least about 10 apertures/$cm^2$, or at least about 25 apertures/$cm^2$.

As can be understood with respect to forming apparatus 103, apertures can be made by mechanically deforming precursor web 25 that can be described as generally planar and two dimensional. By "planar" and "two dimensional" is meant that the precursor web 25 may be flat relative to a finished apertured web 1 having a distinct, out-of-plane, z-direction three-dimensionality imparted due to the formation of truncated generally conical shaped structures 8. "Planar" and "two-dimensional" are not meant to imply any particular flatness, smoothness or dimensionality and a soft, fibrous non-woven web can be planar in its as-made condition.

As precursor web 25 goes through the nip 116, the teeth 110 of roll 104 enter valleys 108 of roll 102 and simultaneously urge material out of the plane of precursor web 25 to form truncated generally conical shaped structures 8 and apertures, the apertures being defined by the rim of the truncated generally conical shaped structures. In effect, teeth 110 "push" through precursor web 25. As the tip of teeth 110 push through precursor web 25 the web material can be urged by the teeth 110 out of the plane of precursor web 25 and can be stretched and/or plastically deformed in the z-direction, creating out-of-plane geometry characterized by conical shaped structures 8 and apertures. The truncated generally conical shaped structures 8 can be thought of as volcano-shaped structures.

Figure 9:
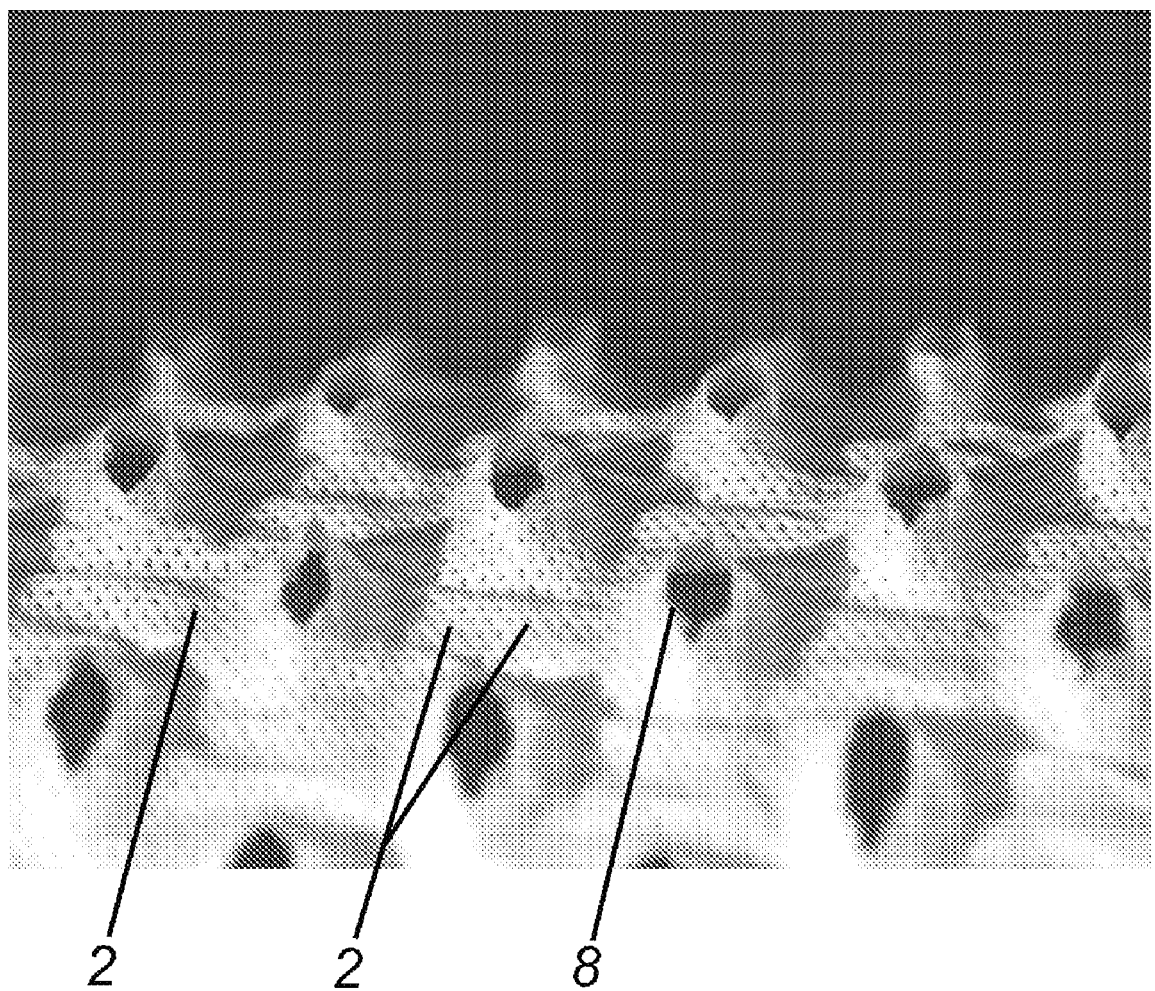
FIG. 9 is an image of a truncated generally conically shaped apertures and aberrations.

FIG. 9 shows an embodiment of a three-dimensional apertured web 1 in which the precursor web 25 was not a flat film but rather was a film that was pre-textured with microscopic aberrations 2. Aberrations 2 can be bumps, embossments, holes, or the like. In the embodiment shown, aberrations 2 are volcano-shaped micro-apertures, formed by a hydroforming process. A suitable hydroforming process is the first phase of the multiphase hydroforming process disclosed in U.S. Pat. No. 4,609,518, issued to Curro et al. on Sep. 2, 1986. The hydroforming screen utilized for the web shown in FIG. 9 was a "100 mesh" screen and the film was obtained from Tredegar Film Products, Terre Haute, Ind. Apertures, defined by the rims of the truncated generally conical shaped structures 8, can be formed by teeth 110 of roll 104 in forming apparatus 103. The truncated generally conical shaped structures 8 can be oriented in a topsheet 20 such that the rims of the truncated generally conical shaped structures are on the body facing side of the topsheet. The truncated generally conical shaped structures 8 can be oriented in a topsheet 20 such that the rims of the truncated generally conical shaped structures are on the garment facing side of the topsheet 20. The truncated generally conical shaped structures 8 can be oriented in a topsheet 20 such that some of the rims of the truncated generally conical shaped structures are on the garment facing side of the topsheet 20 and some of the rims of the truncated generally conical shaped structures are on the body facing side of the topsheet 20. A polymeric web, such as that employed in Always Ultra sanitary napkins, marked by Procter & Gamble Co., Cincinnati, Ohio, or that disclosed in U.S. Pat. No. 7,402,723, issued to Stone et al., Jul. 22, 2008, can be practical for the topsheet 20 or components/portions thereof.

Aberrations 2 can also be non-apertured protrusions or hollow fibrils having an open proximal end and a closed distal end integral with the precursor web 25 to provide texture that provides for a tactile impression of softness. Aberrations 2 other than non-apertured protrusions and fibrils are contemplated. Softness can be beneficial when webs 1 are used as a topsheet in a disposable absorbent article. A soft, compliant topsheet for a disposable absorbent article can be achieved when the apertured web 1 is used with the second side 14 having aberrations 2 as the body-facing surface of the article. In some embodiments, aberrations 2 can be on the garment facing side of the topsheet to possibly provide for a different level of comfort or different properties related to flow of fluids.

The apertures of the film embodiments shown in FIG. 9 were made on an apparatus like that shown in FIG. 7, where the forming apparatus 103 is arranged to have one patterned roll, e.g., roll 104, and one non-patterned roll 102. In certain embodiments nip 116 can be formed by using two patterned rolls having either the same or differing patterns, in the same or different corresponding regions of the respective rolls. Such an apparatus can produce webs with apertures protruding from both sides of the apertured web 1, as well as macro-texture, e.g., aberrations, micro-apertures, or micro-patterns, in the web 1. Likewise, it may be desirable to have multiple forming apparatuses 103 such that apertured web 1 is re-processed to have additional truncated generally conical shaped structures 8 and/or apertures. For example, a greater aperture area density of truncated generally conical shaped structures 8 on apertured web 1 can be achieved by processing precursor web 25 through two or more forming apparatuses 103 or by decreasing the spacing between teeth 110.

Figure 10:
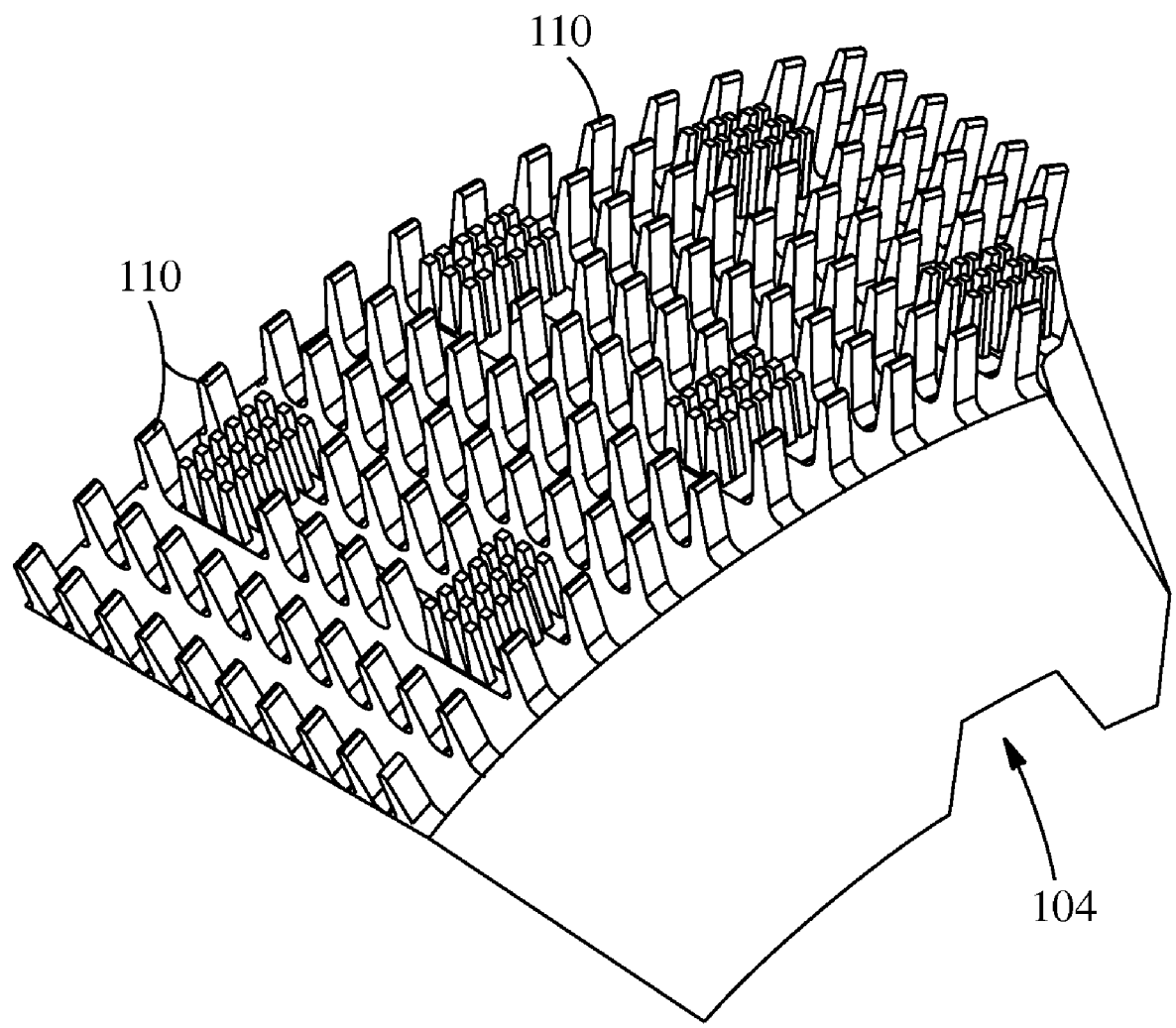
FIG. 10 is a schematic of a roll having different sized teeth and spacing of teeth.

The number, aperture area density, size, geometry, and out of plane geometry associated with the apertures can be varied by changing the number, spacing between, geometry, and size of teeth 110 and making corresponding dimensional changes as necessary to roll 104 and/or roll 102. A topsheet 20 having a first portion 60 having first apertures and second portion 70 having second apertures can be formed using a roll 104 in which different portions of the roll 104 have one size and/or spacing of teeth 110 and other portions of roll 104 have another size and/or spacing of teeth 110. FIG. 10 illustrates a portion of roll 104 in which different areas of the roll 104 have different sizes and/or spacing of teeth 110.

Figure 11:
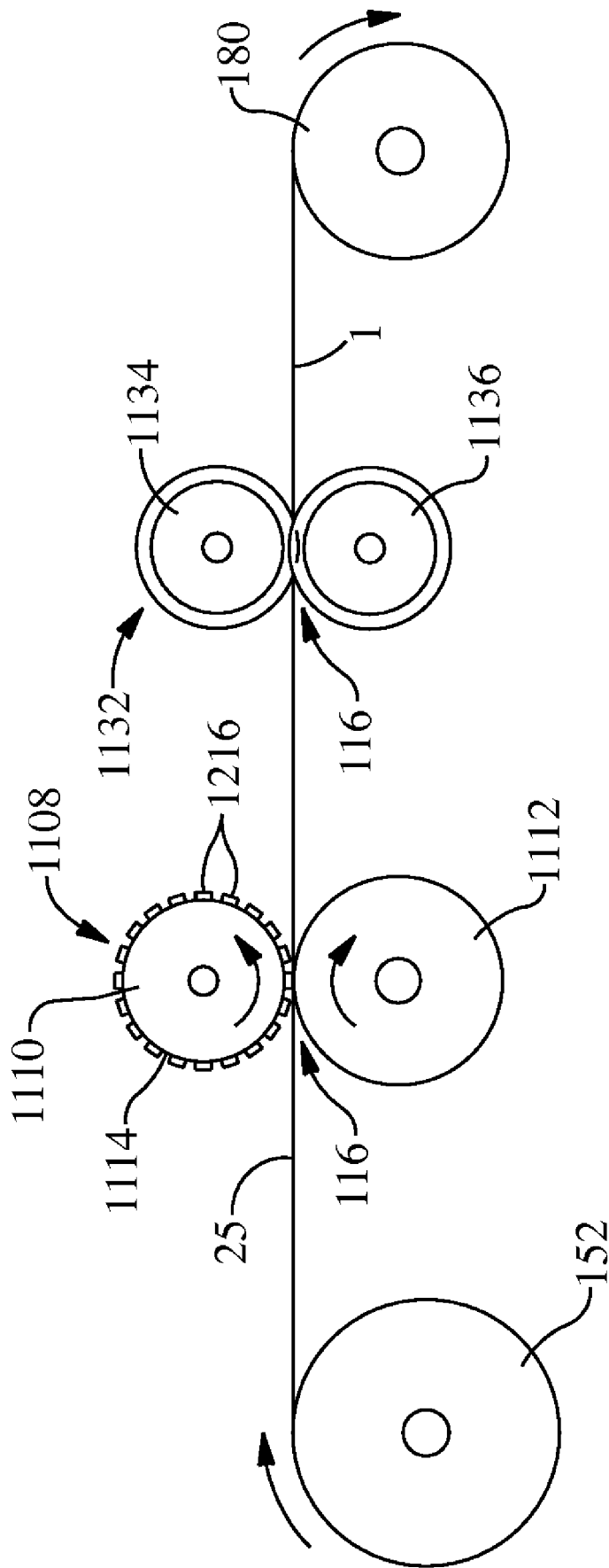
FIG. 11 a schematic of an apparatus for selectively aperturing a nonwoven web.

The topsheet 20 can comprise an apertured nonwoven web. Referring to FIG. 11 there is schematically illustrated a process and apparatus for selectively aperturing a nonwoven web suitable for use as a topsheet on a disposable absorbent article. U.S. patent application Ser. No. 11/249,618, U.S. Pat. Nos. 5,714,107, and 5,628,097 disclose apertures, apparatuses, and methods for creating apertures in nonwoven webs.

Nonwoven precursor web 25 can be unwound from a supply roll 152 and travel in a direction indicated by the arrows associated therewith as the supply roll 152 rotates in the direction indicated by the arrows associated therewith. The nonwoven precursor web 25 passes through a nip 116 of the web weakening roller arrangement 1108 formed by calender roll 1110 and smooth anvil roller 1112.

The nonwoven precursor web 25 may be formed by known nonwoven extrusion processes, such as, for example, known meltblowing processes or known spunbonding processes, and passed directly through the nip 116 without first being bonded and/or stored on a supply roll.

The nonwoven precursor web 25 may be extensible, elastic, or nonelastic. The nonwoven precursor web 25 may be a spunbonded web, a meltblown web, or a bonded carded web. If the nonwoven precursor web 25 is a web of meltblown fibers, it may include meltblown microfibers. The nonwoven precursor web 25 may be made of fiber forming polymers such as, for example, polyolefins. Exemplary polyolefins include one or more of polypropylene, polyethylene, ethylene copolymers, propylene copolymers, and butene copolymers.

In another embodiment, the nonwoven precursor web 25 may be a multilayer material having, for example, at least one layer of a spunbonded web joined to at least one layer of a meltblown web, a bonded carded web, or other suitable material. For example, the nonwoven precursor web 25 may be a multilayer web having a first layer of spunbonded polypropylene having a basis weight from about 0.2 to about 8 ounces per square yard, a layer of meltblown polypropylene having a basis weight from about 0.2 to about 4 ounces per square yard, and a second layer of spunbonded polypropylene having a basis weight from about 0.2 to about 8 ounces per square yard. Alternatively, the nonwoven web may be a single layer of material, such as, for example, a spunbonded web having a basis weight from about 0.2 to about 10 ounces per square yard or a meltblown web having a basis weight from about 0.2 to about 8 ounces per square yard.

The nonwoven precursor web 25 may be joined to a polymeric film to form a laminate. Suitable polymeric film materials include but are not limited to polyolefins, such as polyethylenes, polypropylene, ethylene copolymers, propylene copolymers, and butene copolymers; nylon (polyamide); metallocene catalyst-based polymers; cellulose esters; poly (methyl methacrylate); polystyrene; poly (vinyl chloride); polyester; polyurethane; compatible polymers; compatible copolymers; and blends, laminates and/or combinations thereof.

The nonwoven precursor web 25 may also be a composite made up of a mixture of two or more different fibers or a mixture of fibers and particles. Such mixtures may be formed by adding fibers and/or particulates to the gas stream in which the meltblown fibers or spunbond fibers are carried so that an intimate entangled co-mingling of fibers and other materials, e.g., wood pulp, staple fibers, and particles, occurs prior to collection of the fibers.

The nonwoven precursor web 25 of fibers can be joined by bonding to form a coherent web structure. Suitable bonding techniques include, but are not limited to, chemical bonding, thermobonding, such as point calendering, hydroentangling, and needling.

One or both of the patterned calender roll 1110 and the smooth anvil roller 1112 may be heated and the pressure between the two rollers may be adjusted to provide the desired temperature, if any, and pressure to concurrently weaken and melt-stabilize the nonwoven precursor web 25 at a plurality of locations.

The patterned calender roll 1110 is configured to have a cylindrical surface 1114, and a plurality of protuberances 1216 which extend outwardly from cylindrical surface 1114. The protuberances 1216 are disposed in a predetermined pattern with each protuberance 1216 being configured and disposed to precipitate a weakened, melt-stabilized location in the nonwoven precursor web 25 to create a predetermined pattern of weakened, melt-stabilized locations in the nonwoven precursor web 25. Also shown in FIG. 11 and discussed further below are incremental stretching system 1132, and incremental stretching rollers 1134 and 1136.

Prior to entering nip 116, the coherent nonwoven web can comprise a plurality of fibers joined together by bonds to form a coherent web structure.

Figure 12:
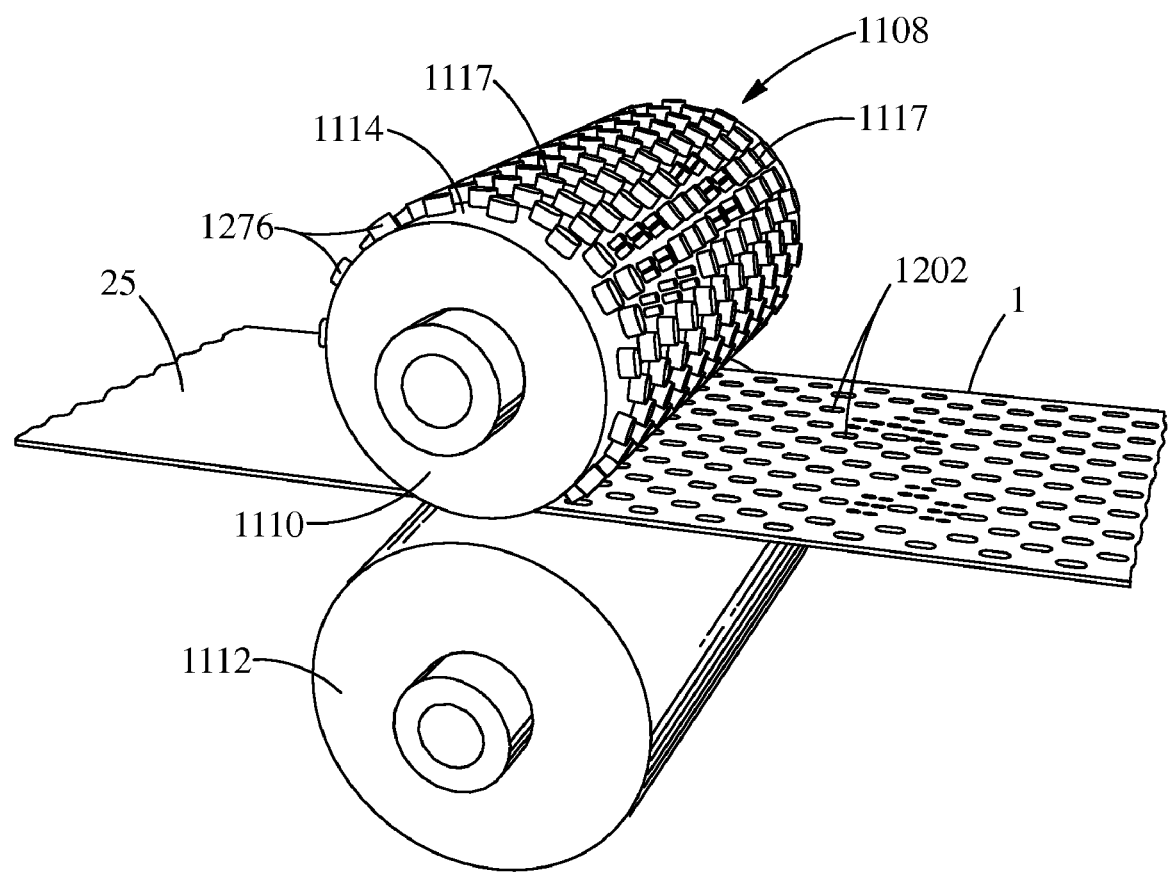
FIG. 12 is a schematic of a weakening roller arrangement.

Patterned calender roll 1110 can have a repeating pattern of protuberances 1216 which extend about the entire circumference of cylindrical surface 1114. Alternatively, the protuberances 1216 may extend around a portion, or portions of the circumference of cylindrical surface 1114. As shown in FIG. 12, the spacing of the protuberances 1216 on one portion of the patterned calender roll 1110 can be different from the spacing of the protuberances 1216 on another part of the patterned calender roll 1110. Arranging the protuberances 1216 in this manner can allow different portions of an apertured web 1, which can form the topsheet 20, to have first and second portions that differ from one another.

By way of example and not to be limiting, protuberances 1216 can be truncated conical shapes which extend radially outwardly from cylindrical surface 1114 and which have elliptical distal end surfaces 1117. Other suitable shapes for distal end surfaces 1117 include, but are not limited to circular, square, rectangular, etc. The patterned calender roll 1110 can be finished so that all of the end surfaces 1117 lie in an imaginary right circular cylinder which is coaxial with respect to the axis of rotation of calender roll 1110.

Protuberances 1216 can be blades having their long axis oriented circumferentially about the patterned calender roll 1110. Protuberances 1216 can be blades having their long axis oriented parallel to the rotating axis of the calender roll 1110.

The protuberances may be disposed in any predetermined pattern about patterned calender roll 1110. After passing through the weakening roller arrangement 1108, the precursor web 25 can have a plurality of melt stabilized locations 1202. Anvil roller 1112, can be a smooth surfaced, right circular cylinder of steel.

Figure 13:
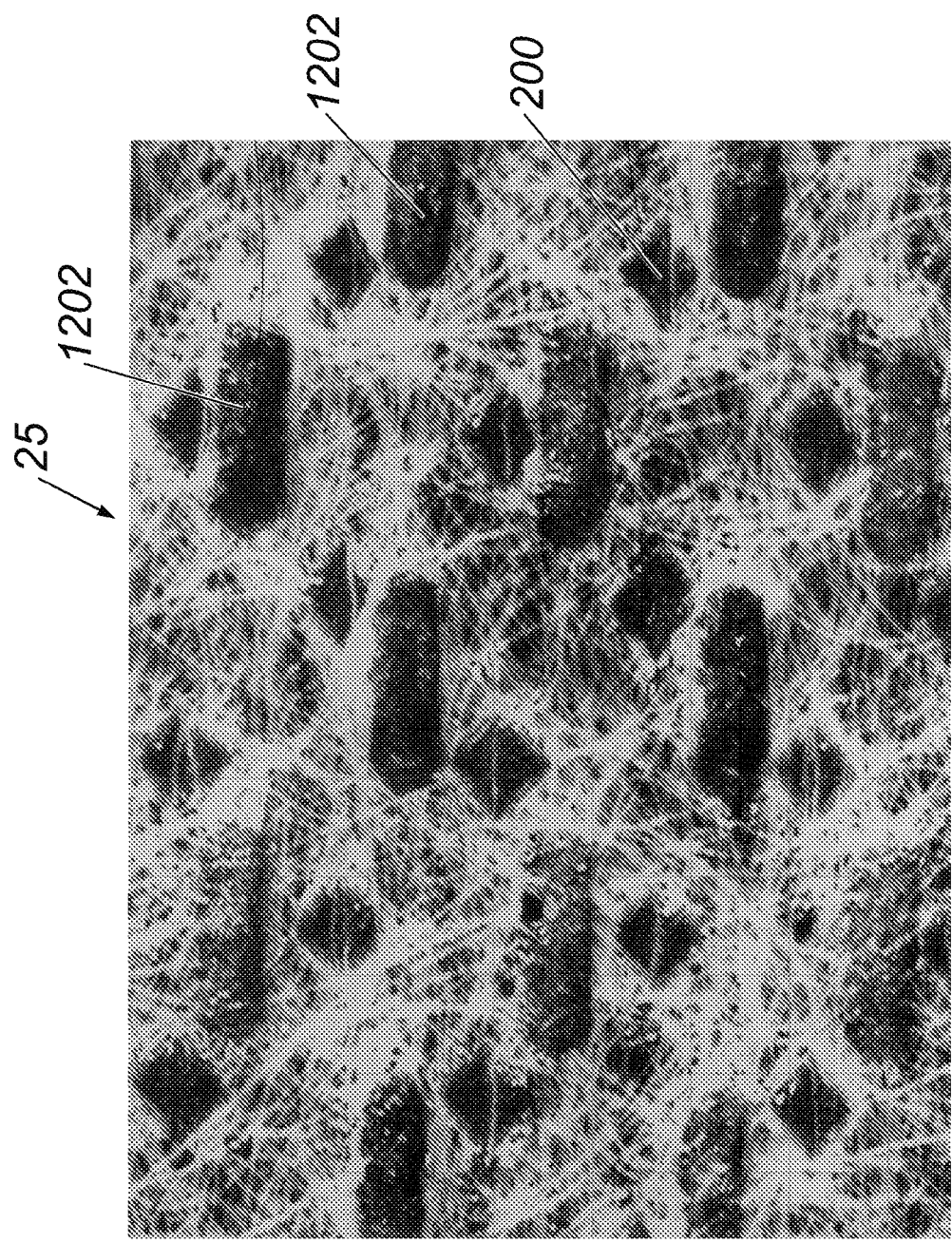
FIG. 13 is an illustration of a nonwoven web after passing through the weakening roller arrangement.

FIG. 13 is a photograph of the nonwoven precursor web 25 after having passed through the weakening roller arrangement 1108, and prior to passing through the nip 116 of the incremental stretching system 1132. As can be seen in the photograph, the nonwoven precursor web 25 includes a plurality of weakened, melt-stabilized locations 1202. Weakened, melt-stabilized locations 1202 generally correspond to the pattern of protuberances 1216 extending from the cylindrical surface 1114 of patterned calender roll 1110. As shown in FIG. 13, the nonwoven precursor web 25 also includes coherent web forming point calendered bonds 200 which can serve to maintain the structural integrity of the nonwoven precursor web 25.

From the weakening roller arrangement 1108, the nonwoven precursor web 25 passes through nip 116 formed by the incremental stretching system 1132 employing opposed pressure applicators having three-dimensional surfaces which at least to a degree are complementary to one another.

Figure 14:
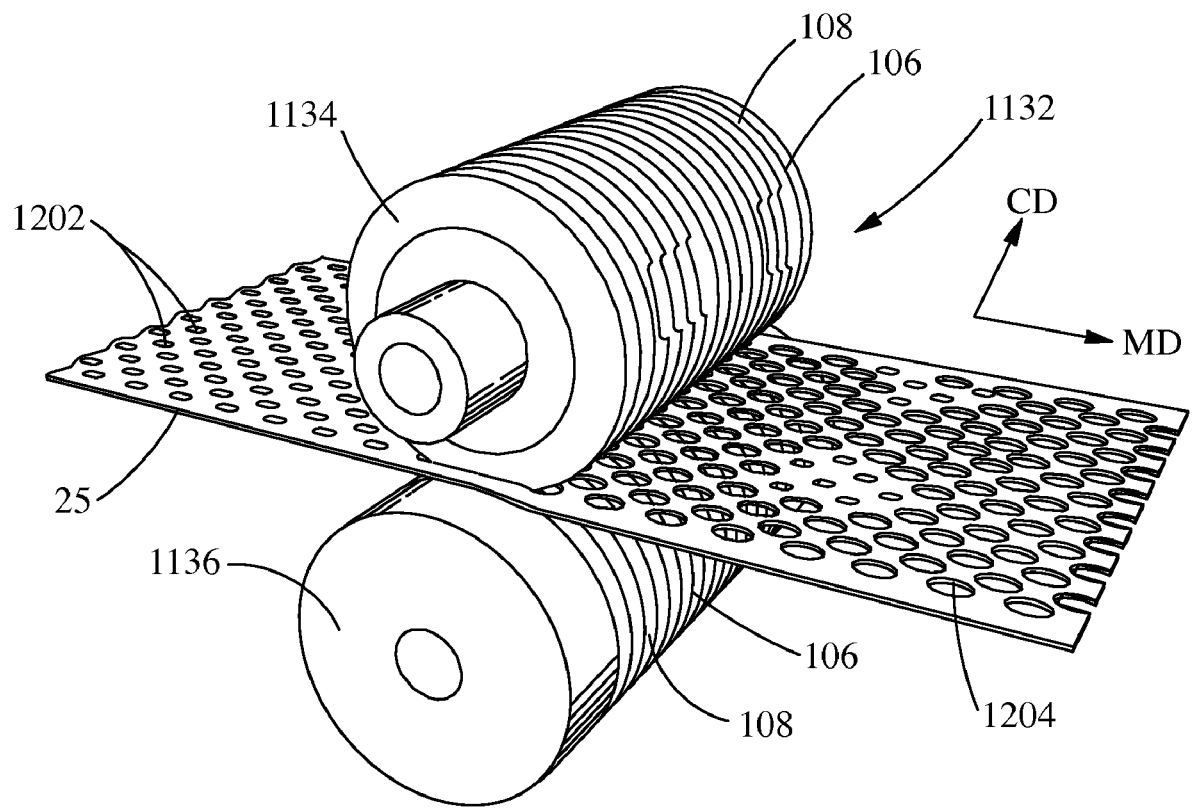
FIG. 14 is a schematic of a stretching system.

Referring now to FIG. 14, there is shown a fragmentary enlarged view of the incremental stretching system 1132 comprising incremental stretching rollers 1134 and 1136. The incremental stretching roller 1134 can comprise a plurality of ridges 106 and corresponding valleys 108 that extend about the entire circumference of incremental stretching roller 1134 or only partially about the circumference of incremental stretching roller 1134. Incremental stretching roller 1136 includes a plurality of complimentary ridges 106 and a plurality of corresponding valleys 108. The ridges 106 on incremental stretching roller 1134 intermesh with or engage the valleys 108 on incremental stretching roller 1136 and the ridges 106 on incremental stretching roller 1136 intermesh with or engage the valleys 108 on incremental stretching roller 1134. As the nonwoven precursor web 25 having weakened, melt-stabilized locations 1202 passes through the incremental stretching system 1132, the nonwoven precursor web 25 is subjected to tensioning in the CD or cross-machine direction causing the nonwoven precursor web 25 to be extended in the CD direction. Alternatively, or additionally, the nonwoven precursor web 25 may be tensioned in the MD or machine direction. The tensioning force placed on the nonwoven precursor web 25 can be adjusted such that it causes the weakened, melt-stabilized locations 1202 to rupture creating a plurality of formed SAN apertures 1204 (SAN standing for Stretch Apertured Nonwoven) coincident with the weakened melt-stabilized locations 1202 in the nonwoven precursor web 25 to form apertured web 1. However, the bonds of the nonwoven precursor web 25 can be strong enough such that they do not rupture during tensioning, thereby maintaining the nonwoven web in a coherent condition even as the weakened, melt-stabilized locations rupture.

As shown in FIG. 14, different portions of incremental stretching rollers 1134 and 1136 can have different depth of valleys 108 and height of ridges 106 about the circumference of incremental stretching roller 1136 and incremental stretching roller 1134. The distance between valleys 108 and ridges 106 and incremental stretching rollers 1134 and 1136 can also be varied. Configuring the rolls in this manner will allow different amounts of stretching to be applied to different portions of the nonwoven precursor web 25, thereby forming an apertured web 1 having portions that differ from one another which can be used for topsheet 20.

Figure 15:
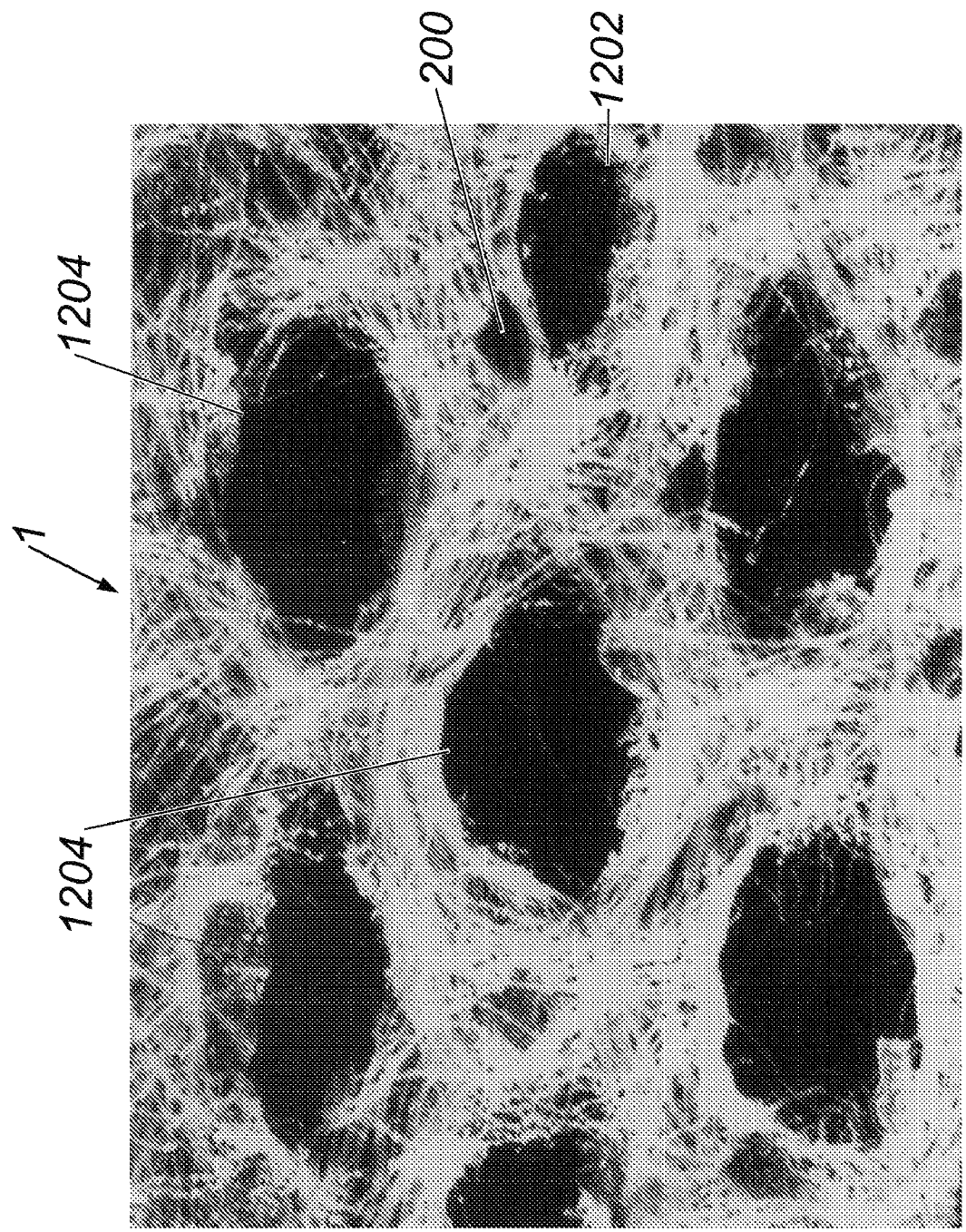
FIG. 15 is an image of a stretch apertured nonwoven.

Referring now to FIG. 15 there is shown a photograph of the apertured web 1 after the precursor web 25 has been subjected to the tensioning force applied by the incremental stretching system 1132. As can be seen in the photograph, the apertured web 1 has a plurality of SAN apertures 1204 which are coincident with the weakened, melt-stabilized locations 1202 of the nonwoven precursor web 25, shown in FIG. 13.

Other structures of incremental stretching mechanisms suitable for incrementally stretching or tensioning the nonwoven web are described in International Patent Publication No. WO 95/03765, published Feb. 9, 1995, in the name of Chappell, et al.

The nonwoven apertured web 1 can be taken up on wind-up roll 180 and stored. Alternatively, the nonwoven apertured web 1 may be fed directly to a production line where it is used to form a topsheet on a disposable absorbent article.

Figure 16:
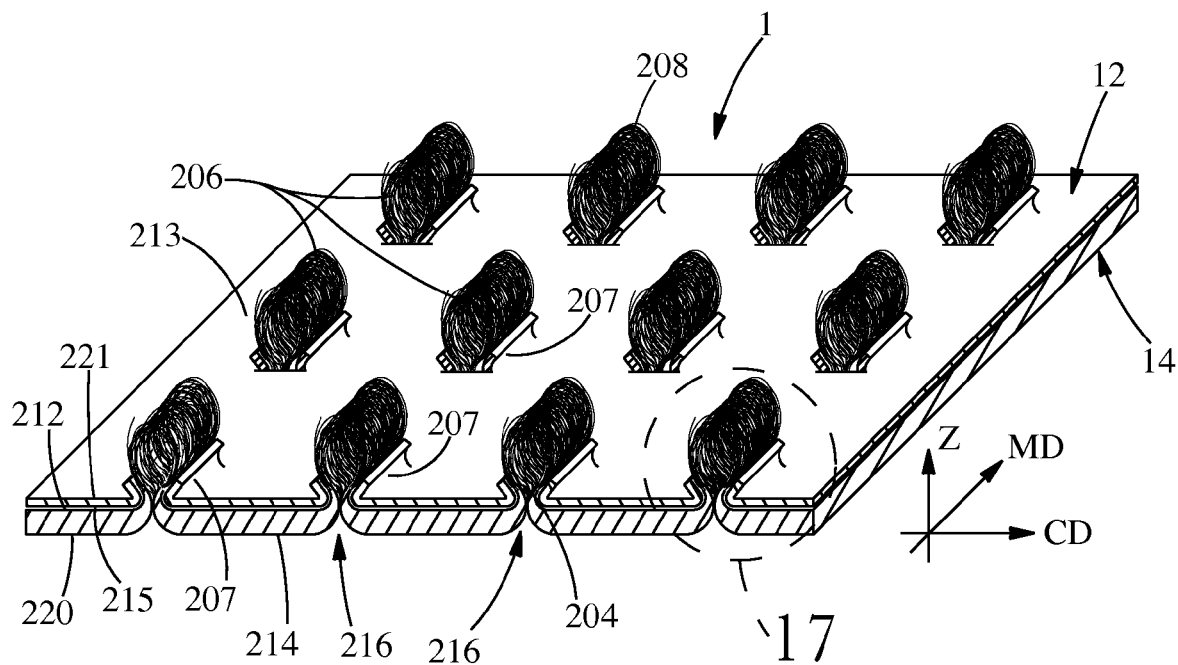
FIG. 16 is a schematic of a web having tufts.

The first portion 60 and/or the second portion 70 can comprise tufts 206 illustrated in FIG. 16. Tufts 206 can comprise a laminate web 1 comprised of two or more layers in which one of the layers is pushed into the other layer or protrudes through apertures in the other layer, an example of which is shown in FIG. 16. The layers are referred to herein as generally planar, two-dimensional precursor webs, such as first precursor web 220 and second precursor web 221. Either precursor web can be a film, a nonwoven, or a woven web. First precursor web 220 and second precursor web 221 (and any additional webs) can be joined with or without adhesive, thermal bonding, ultrasonic bonding and the like. First precursor web 220 and second precursor web 221 can correspond to the lower layer 22 and upper layer 21, respectively, of topsheet 20, as shown in FIG. 1.

Web 1 has a first side 12 and a second side 14, the term "sides" being used in the common usage of generally planar two-dimensional webs, such as paper and films that have two sides when in a generally flat condition. First precursor web 220 has a first precursor web first surface 212 and a first precursor web second surface 214. Second precursor web 221 has a second precursor web first surface 213 and a second precursor web second surface 215. Web 1 has a machine direction (MD) and a cross machine direction (CD) as is commonly known in the art of web manufacture. The first precursor web 220 can be a nonwoven web comprised of substantially randomly oriented fibers, a polymer film, or a woven web. By "substantially randomly oriented" is meant that, due to processing conditions of the precursor web, there may be a higher amount of fibers oriented in the MD than the CD, or vice-versa. Second precursor web 221 can be a nonwoven web similar to the first precursor web 220, or a polymer film or an apertured polymer film, such as a polyethylene film.

Figure 17:
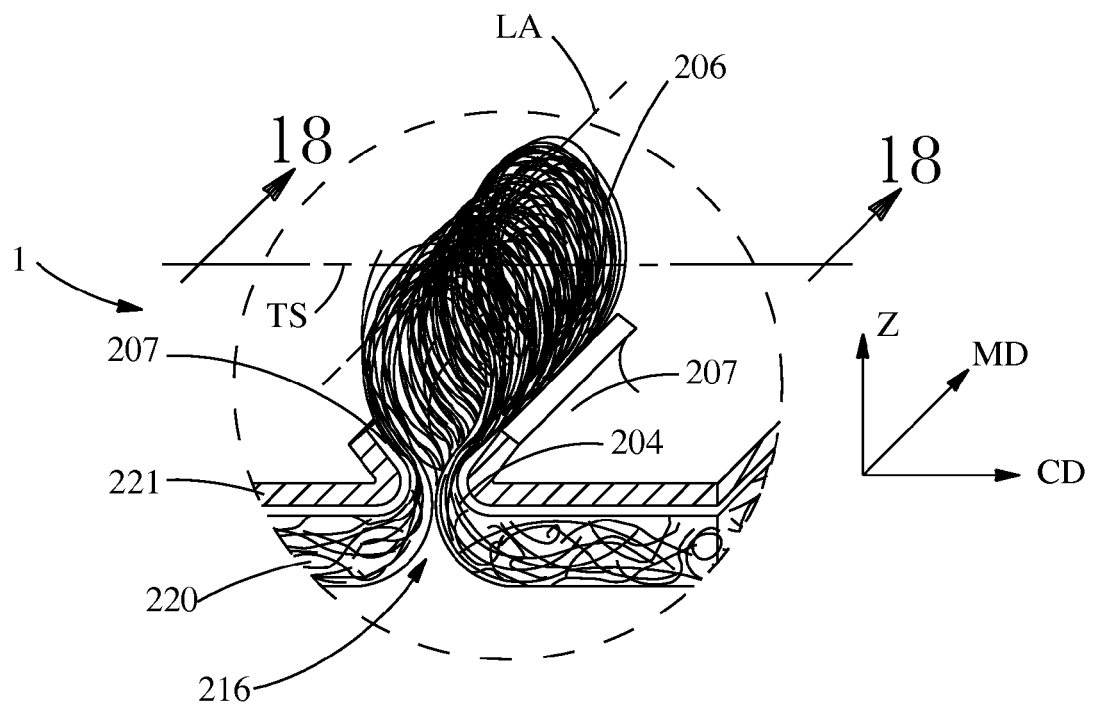
FIG. 17 is a cutaway section of a web having tufts as indicated by Cutaway 17 in FIG. 16.

In one embodiment, first side 12 of web 1 is defined by exposed portions of the second precursor web first surface 213 and one or more discrete tufts 206, which can be discrete tufts 206, which are integral extensions of the fibers of a nonwoven first precursor web 220. Tufts 206 can protrude through apertures in the second precursor web 221. As shown in FIG. 17, each tuft 206 can comprise a plurality of looped fibers 208 extending through second precursor web 221 and outwardly from the second precursor web first surface 213 thereof.

Tufts can be formed by urging fibers out-of-plane in the z-direction at discrete, localized, portions of first precursor web 220.

First precursor web 220 can be a fibrous woven or nonwoven web comprising elastic or elastomeric fibers. Elastic or elastomeric fibers can be stretched at least about 50% and return to within 10% of their original dimension. Tufts 206 can be formed from elastic fibers if the fibers are simply displaced due to the mobility of the fiber within the nonwoven, or if the fibers are stretched beyond their elastic limit and are plastically deformed.

Second precursor web 221 can be virtually any web material, the only requirement being that it have sufficient integrity to be formed into the laminate by the process described below, and that it have elongation properties relative to first precursor web 220, such that upon experiencing the strain of fibers from first precursor web 220 being urged out-of-plane in the direction of second precursor web 221, second precursor web 221 will be urged out of plane (e.g. by stretching) or rupture (e.g.

by tearing due to extensional failure). If rupture occurs, IPS apertures 204 can be formed at the rupture locations (IPS stands for Inter-Penetrating Self). Portions of first precursor web 220 can extend through IPS apertures 204 (i.e., "push through" or protrude through) in second precursor web 221 to form tufts 206 on first side 12 of web 1. In one embodiment second precursor web 221 is a polymer film. Second precursor web 221 can also be a woven textile web, a nonwoven web, a polymer film, an apertured polymer film, a paper web, (e.g., tissue paper), a metal foil (e.g., aluminum wrapping foil), a foam (e.g., urethane foam sheeting), or the like.

As shown in FIGS. 16 and 17, tufts 206 can extend through IPS apertures 204 in second precursor web 221. IPS apertures 204 can be formed by locally rupturing second precursor web 221. Rupture may involve a simple splitting open of second precursor web 221, such that IPS apertures 204 are in-plane (MD-CD) two-dimensional apertures. However, for some materials, such as polymer films, portions of second precursor web 221 can be deflected or urged out-of-plane (i.e., the plane of second precursor web 221) to form flap-like structures, referred to herein as a flap, or flaps, 207. The form and structure of flaps 207 can be dependent upon the material properties of second precursor web 221. Flaps 207 can have the general structure of one or more flaps, as shown in FIGS. 16 and 17. In other embodiments, flap 207 can have a more volcano shaped structure, as if the tuft 206 is erupting from the flap 207.

Tufts 206 can be, in a sense, "pushed through" (or protrude through) second precursor web 221 and can be "locked" in place by frictional engagement with IPS apertures 204. This indicates a certain amount of recovery at the opening that tends to constrain tuft 206 from pulling back out through IPS apertures 204. The frictional engagement of the tufts and openings can provide for a laminate web structure having tufting on one side that can be formed without adhesives or thermal bonding.

Tufts 206 can be spaced sufficiently closely so as to substantially cover (for example cover more than about 85% the area, fraction portion, or zone of interest) first side 12 of web 1 when tufts 206 protrude through second precursor web 221. In such an embodiment, both sides of web 1 appear to be nonwoven, with a difference between first side 12 and second side 14 being a difference in surface texture. Therefore, in one embodiment, the web 1 can be described as a laminate material of two or more precursor webs, wherein both sides of the laminate web are substantially covered by fibers from only one of the precursor webs.

The looped fibers 208 can be substantially aligned such that tuft 206 has a distinct linear orientation and a long axis LA, as shown in FIG. 17. Tufts 206 can also have a short axis TS generally orthogonal to long axis LA in the MD-CD plane the MD-CD plane able to be considered as encompassing the first precursor web 220 and second precursor web 221 and tufts 206). In the embodiment shown in FIGS. 17 and 18, long axis LA is parallel to the MD. The tuft 206 can have a symmetrical shape in the MD-CD plane, such as a circular shape or square shape. Tufts 206 can have an aspect ratio (ratio of longest dimension to shortest dimension, both measured in the MD-CD plane) greater than 1. In one embodiment, all the spaced apart tufts 206 have generally parallel long axes LA. The number of tufts 206 per unit area of web 1, i.e., the area density of tufts 206, can be varied from about 1 tuft/cm$^2$ to about 100 tufts/cm$^2$. There can be at least about 10, or at least about 20 tufts/cm$^2$.

Figure 18:
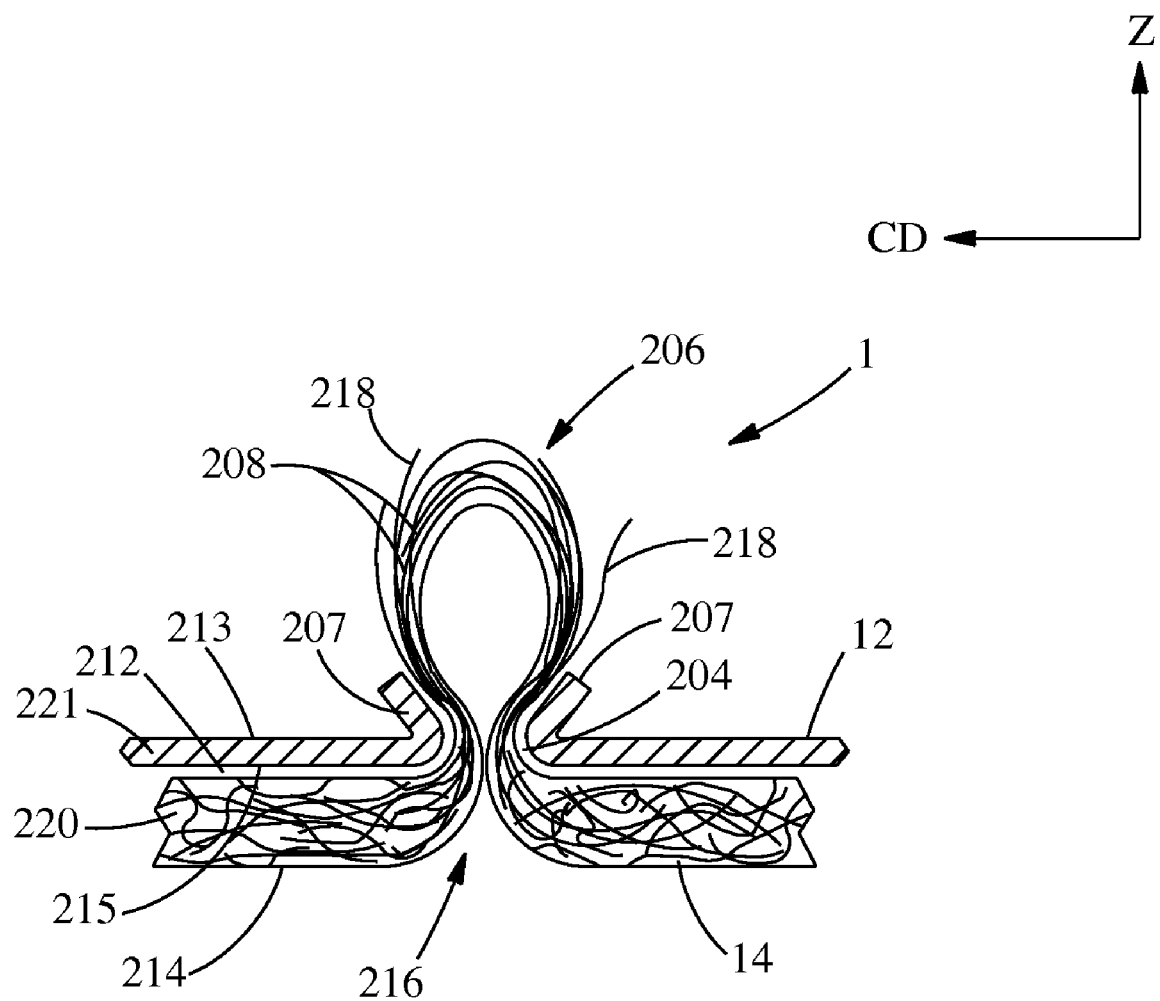
FIG. 18 is a cross section of a web having tufts as indicated by Section 18-18 in FIG. 17.

In another embodiment, each tuft 206 can comprise a plurality of non-looped fibers 218 (as shown in FIG. 18) that extend outwardly from the second precursor web first surface 213. In general, the looped fibers 208 or non-looped fibers 218 of the tufts 206 comprise fibers that are integral with and extend from the fibers of the first precursor web 220.

Figure 19:
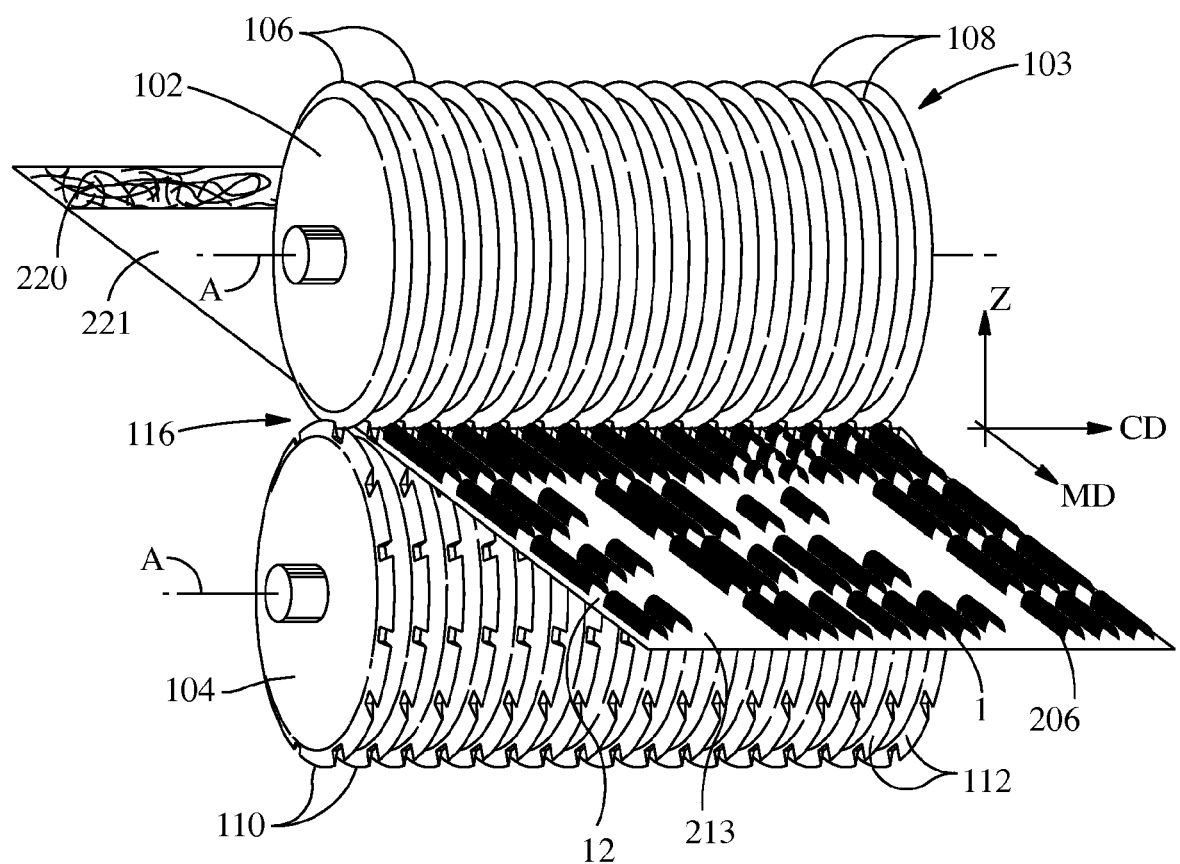
FIG. 19 is a schematic of an apparatus for forming a web having tufts.

Referring to FIG. 19 there is shown an apparatus and method for making a web 1 comprising tufts 206. The forming apparatus 103 comprises a pair of intermeshing rolls 102 and 104, each rotating about an axis A, the axes A being parallel in the same plane. Roll 102 comprises a plurality of ridges 106 and corresponding valleys 108 which can extend unbroken about the entire circumference of roll 102. Roll 104 can comprise a plurality of rows of circumferentially-extending ridges that have been modified to be rows of circumferentially-spaced teeth 110 that extend in spaced relationship about at least a portion of roll 104. Portions of roll 104 can be without teeth 110 to permit forming a web 1 having portions without tufts 206. Size and/or spacing of teeth 110 can be varied, as shown in FIG. 19, to permit formation of a web 1 having different size tufts 206 in different portions and/or have portions without tufts 206.

The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the valleys 108 of roll 102. Both or either of rolls 102 and 104 can be heated by means known in the art such as by using hot oil filled rollers or electrically-heated rollers.

In FIG. 19, the forming apparatus 103 is shown as having one patterned roll, e.g., roll 104, and one non-patterned grooved roll 102. Two patterned rolls 104 having either the same or differing patterns, in the same or different corresponding regions of the respective rolls can be used. Such an apparatus can produce webs having tufts 206 protruding from both sides of the web 1. An apparatus can be designed to have teeth pointing in opposite directions on the same roll. This can result in a web with tufts 206 being produced on both sides of the web.

Web 1 can be made by mechanically deforming precursor webs, such as first precursor web 220 and second precursor web 221, that can each be described as generally planar and two dimensional prior to processing by the apparatus shown in FIG. 19. By "planar" and "two dimensional" is meant that the webs start the process in a generally flat condition relative to the web 1 that has distinct, out-of-plane, z-direction three-dimensionality due to the formation of tufts 206. "Planar" and "two-dimensional" are not meant to imply any particular flatness, smoothness or dimensionality.

The process and apparatus for forming tufts 206 is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". As described below, the teeth 110 of roll 104 have a geometry associated with the leading and trailing edges that permit the teeth to essentially "push" through the plane of the first precursor web 220 and second precursor web 221. In a two layer laminate web, the teeth 110 urge fibers from a first precursor web 220 simultaneously out-of-plane and through the plane of second precursor web 221. Therefore, tufts 206 of web 1 can be "tunnel-like" tufts of looped fibers 208 extending through and away from the second precursor web first surface 213 and can be symmetrically shaped.

First precursor web 220 and second precursor web 221 are provided either directly from their respective web making processes or indirectly from supply rolls and moved in the machine direction to the nip 116 of counter-rotating intermeshing rolls 102 and 104. The precursor webs are preferably held in a sufficient web tension so as to enter the nip 116 in a generally flattened condition by means well known in the art of web handling. As first precursor web 220 and second precursor web 221 pass through the nip 116, the teeth 110 of roll 104 which are intermeshed with valleys 108 of roll 102 simultaneously urge portions of first precursor web 220 out of the plane of first precursor web 220, and in some instances, through second precursor web 221 to form tufts 206. In effect, teeth 110 "push" fibers of first precursor web 220 into or through the plane of the second precursor web 221.

As the tip of teeth 110 push into or through first precursor web 220 and second precursor web 221, the portions of the fibers of first precursor web 220 that are oriented predominantly in the CD across teeth 110 are urged by the teeth 110 out of the plane of first precursor web 220. Fibers can be urged out of plane due to fiber mobility, or they can be urged out of plane by being stretched and/or plastically deformed in the z-direction. Portions of first precursor web 220 urged out of plane by teeth 110 push into or through second precursor web 221, which can rupture due to its relatively lower extensibility, thereby resulting in formation of tufts 206 on first side 12 of web 1.

For a given maximum strain (e.g., the strain imposed by teeth 110 of forming apparatus 103), second precursor web 221 can actually fail under the tensile loading produced by the imposed strain. That is, for the tufts 206 to be disposed on the first side 12 of web 1, second precursor web 221 must have sufficiently low fiber mobility (if any) and/or relatively low elongation-to-break such that it locally (i.e., in the area of strain) fails in tension, thereby producing IPS apertures 204 through which tufts 206 can extend.

In one embodiment, second precursor web 221 has an elongation to break in the range of 1%-5%. While the actual required elongation to break depends on the strain to be induced to form web 1, it is recognized that in some embodiments, second precursor web 221 can exhibit a web elongation-to-break of about 6%, about 7%, about 8%, about 9%, about 10%, or more. It is also recognized that actual elongation-to-break can depend on the strain rate, which, for the apparatus shown in FIG. 19, is a function of line speed. Elongation to break of webs can be measured by means known in the art, such as by standard tensile testing methods using standard tensile testing apparatuses, such as those manufactured by Instron, MTS, Thwing-Albert, and the like.

Furthermore, relative to first precursor web 220, second precursor web 221 can have lower fiber mobility (if any) and/or lower elongation-to-break (i.e., elongation-to-break of individual fibers, or, if a film, elongation-to-break of the film) such that, rather than extending out-of-plane to the extent of the tufts 206, second precursor web 221 can fail in tension under the strain produced by the formation of tufts 206, e.g., by the teeth 110 of forming apparatus 103. In one embodiment, second precursor web 221 exhibits sufficiently low elongation-to-break relative to first precursor web 220 such that flaps 207 of IPS apertures 204 only extend slightly out-of-plane, if at all, relative to tufts 206. Second precursor web 221 can have an elongation to break of at least about 10% less than the first precursor web 220, or at least about 30% less, or at least about 50% less, or at least about 100% less than that of first precursor web 220.

Figure 20:
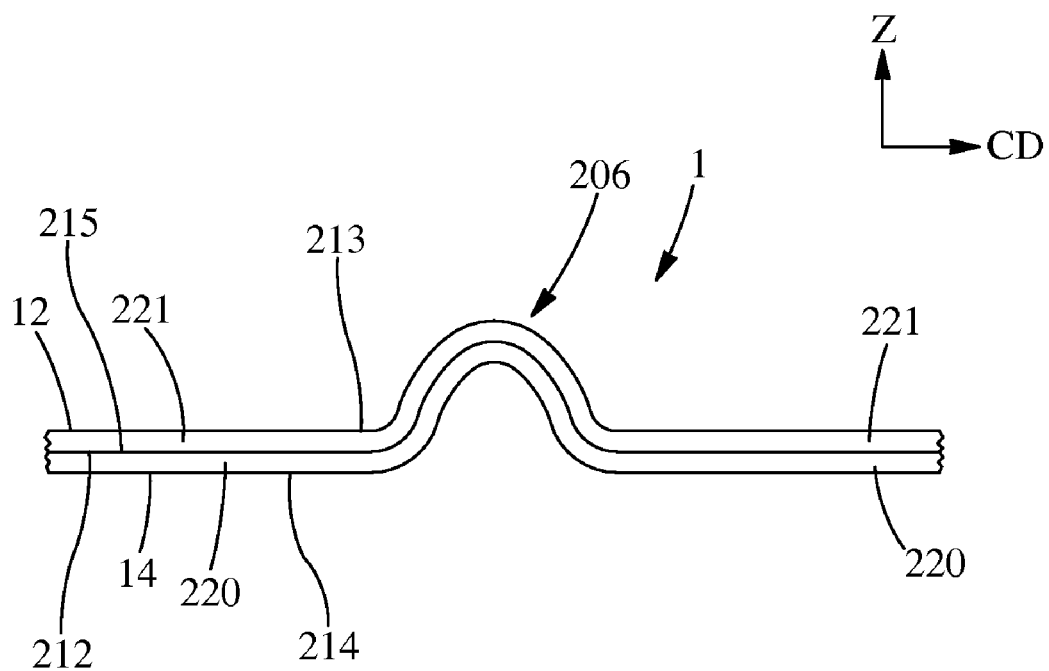
FIG. 20 is a schematic of a tufted web.
Figure 21:
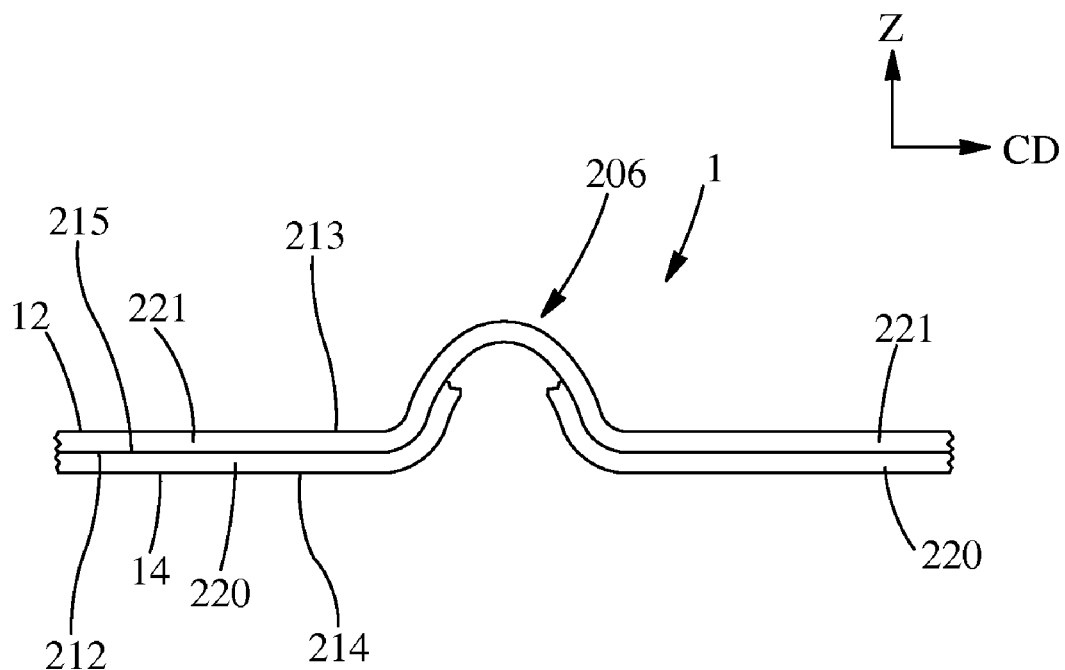
FIG. 21 is schematic of a tufted web.

If second precursor web 221 merely deforms or stretches in the region of induced strain, but does not actually fail, a tuft 206 that does not protrude through second precursor web 221 can be formed, as shown in FIGS. 20 and 21. Tufts 206 illustrated in FIGS. 20 and 21 are in effect nested in the second precursor web 221. As shown in FIG. 20, first precursor web 220 can be pushed into the MD-CD plane of the second precursor web 221 without rupturing second precursor web 221 or tearing first precursor web 220. In essence, first precursor web 220 is indented into second precursor web 221 to form tuft 206. As shown in FIG. 21, first precursor web 220 can be indented into and nested within second precursor web 221 and first precursor web 220 can be ruptured to form tuft 206.

The number, spacing, and size of tufts 206 can be varied by changing the number, spacing, and size of teeth 110 and making corresponding dimensional changes as necessary to roll 104 and/or roll 102. This variation, together with the variation possible in first precursor web 220 and second precursor web 221 permits many varied webs 1 to be made for many purposes such as personal care items, as disclosed in WO 01/76523. A web 1 comprising a nonwoven/film first precursor web/second precursor web combination can also be used as a component in disposable absorbent articles.

A tufted web 1 can be formed from a nonwoven first precursor web 220 having a basis weight of between about 60 gsm and 100 gsm (80 gsm being practical) and a polyolefinic film (e.g., polyethylene or polypropylene) second precursor web 221 having a density of about 0.91-0.94 g/cm$^3$ and a basis weight of about 20 gsm.

Figure 22:
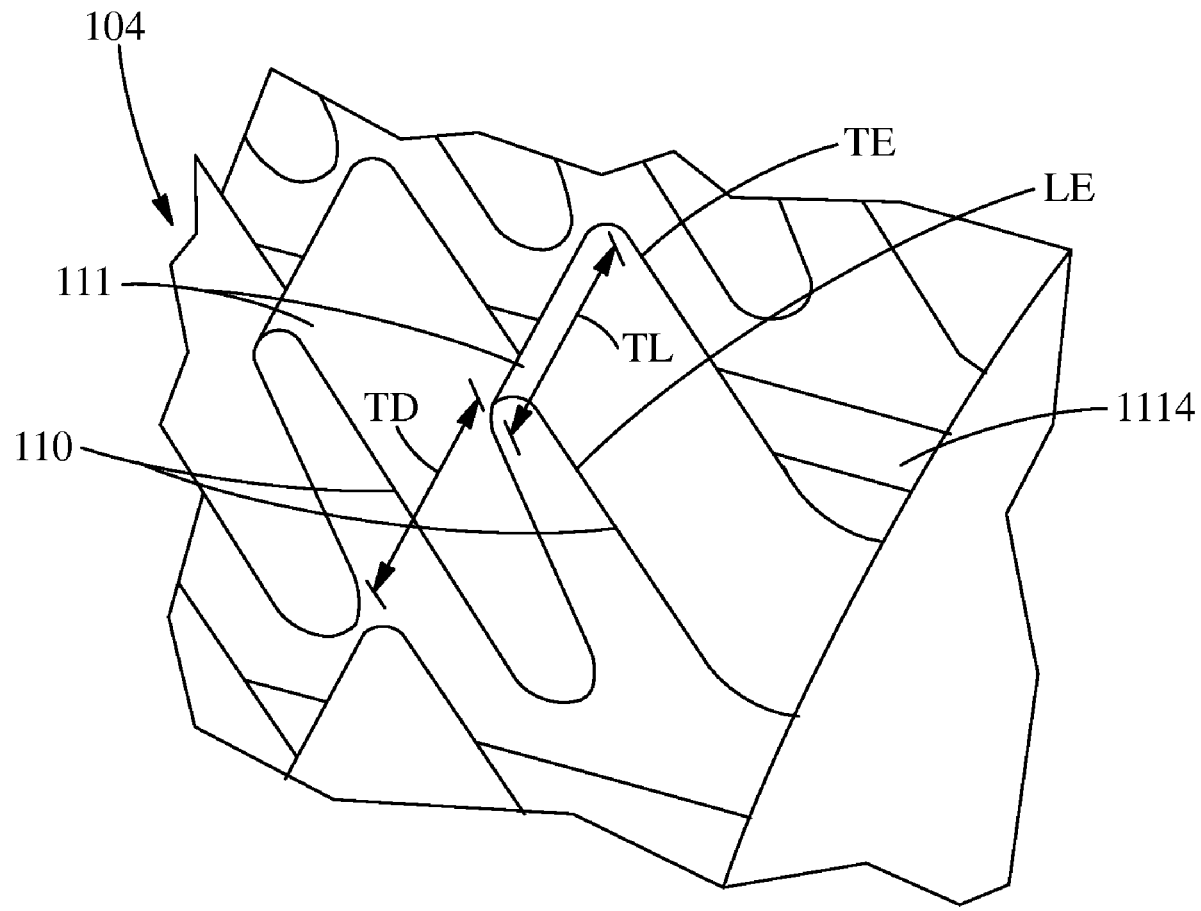
FIG. 22 is a schematic of a roll having teeth.

An enlarged view of teeth 110 is shown in FIG. 22. Teeth 110 can have a circumferential length dimension TL measured generally from the leading edge LE to the trailing edge TE at the tooth tip 111 of about 1.25 mm and can be uniformly spaced from one another circumferentially by a distance TD of about 1.5 mm. For making a web 1 from precursor web 25 having a total basis weight in the range of about 60 to about 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 5 mm (0.200 inches). Depth of engagement E can be from about 0.5 mm to about 5 mm (up to a maximum equal to tooth height TH). Of course, E, P, TH, TD and TL can be varied independently of each other to achieve a desired size, spacing, and area density of tufts 206.

The tooth tip 111 can be elongated and can have a generally longitudinal orientation, corresponding to a long axes LA of tufts 206 and discontinuities 216. It is believed that to get the tufted, looped tufts 206 of the web 1 that can be described as being terry cloth-like, the LE and TE should be very nearly orthogonal to the cylindrical surface 1114 of roll 104. As well, the transition from the tip 111 and LE or TE should be a sharp angle, such as a right angle, having a sufficiently small radius of curvature such that teeth 110 can push through second precursor web 221 at the LE and TE. Without being bound by theory, it is believed that having relatively sharply angled tip transitions between the tip of tooth 110 and the LE and TE permits the teeth 110 to push through first precursor web 220 and second precursor web 221 "cleanly", that is, locally and distinctly, so that the first side 12 of the resulting web 1 has tufts 206. When so processed, the web 1 may not be imparted with any particular elasticity, beyond what the first precursor web 220 and second precursor web 221 may have possessed originally. The pushing through of the second precursor web 221 can result in a small portion of the second precursor web 221 forming "confetti" or small pieces.

Web 1 having tufts 206 can be used as a topsheet 20 or a portion of topsheet 20 of absorbent article 10. Web 1 having tufts 206 can be beneficial as a topsheet 20 for absorbent articles due to the combination of excellent fluid acquisition and distribution to the absorbent core 40, and excellent prevention of rewet to the body-facing surface of topsheet 20 when in use. Rewet can be a result of at least two causes: (1)

squeezing out of the absorbed fluid due to pressure on the absorbent article 10; and/or (2) wetness entrapped within or on the topsheet 20.

Surface texture in various portions of the topsheet 20 can be created by providing tufts 206. Tufts 206 can be oriented such that tufts 206 comprise a portion of the body facing surface 23 of the topsheet 20. Tufts 206 can be oriented such that tufts 206 are oriented on the garment facing surface of the topsheet 20.

A topsheet 20 can be made by using a nonwoven first precursor web 220 and a fluid impermeable or fluid permeable polyethylene film second precursor web 221. The basis weights of the component webs can be varied, however, in general due to cost and benefit considerations a total basis weight of between about 20 gsm and 80 gsm can be desirable for web 1. When made as a film/nonwoven laminate, web 1 can combine the softness and fluid capillarity of fiber tufts and the rewet prevention of a fluid impermeable polymer film.

The first portion 60 can comprise tufts 206. The second portion 70 can comprise tufts 206. The first portion 60 and the second portion 70 can both comprise tufts 206, wherein the tufts in the first portion 60 differ from the tufts in the second portion 70. The difference in the tufts 206 can be the size of the tuft in the out-of-plane dimension, z. The difference in the tufts 206 can be the size or shape of the tuft in the MD-CD plane. The size of a tuft is the largest dimension of the tuft in a plane parallel to the MD-CD plane (presented to the viewer of the topsheet). The difference in the tufts 206 can be the form of the tuft 206 with respect to whether or not the tuft 206 protrudes through the second precursor web 221 or is nested within second precursor web 221. The difference in the tufts 206 can be the color of the tufts 206. Different colors of tufts 206 can help the wearer understand that different portions of the absorbent article 10 may perform differently, help her position the absorbent article 10 properly in her panty, and provide for emotional confidence.

In one example embodiment, the absorbent core 40 can be between a laminate web comprising first precursor web 220 and second precursor web 221 such that neither the first precursor web 220 nor the second precursor web 221 or a part of either web is between the absorbent core 40 and backsheet 30.

Figure 23A:
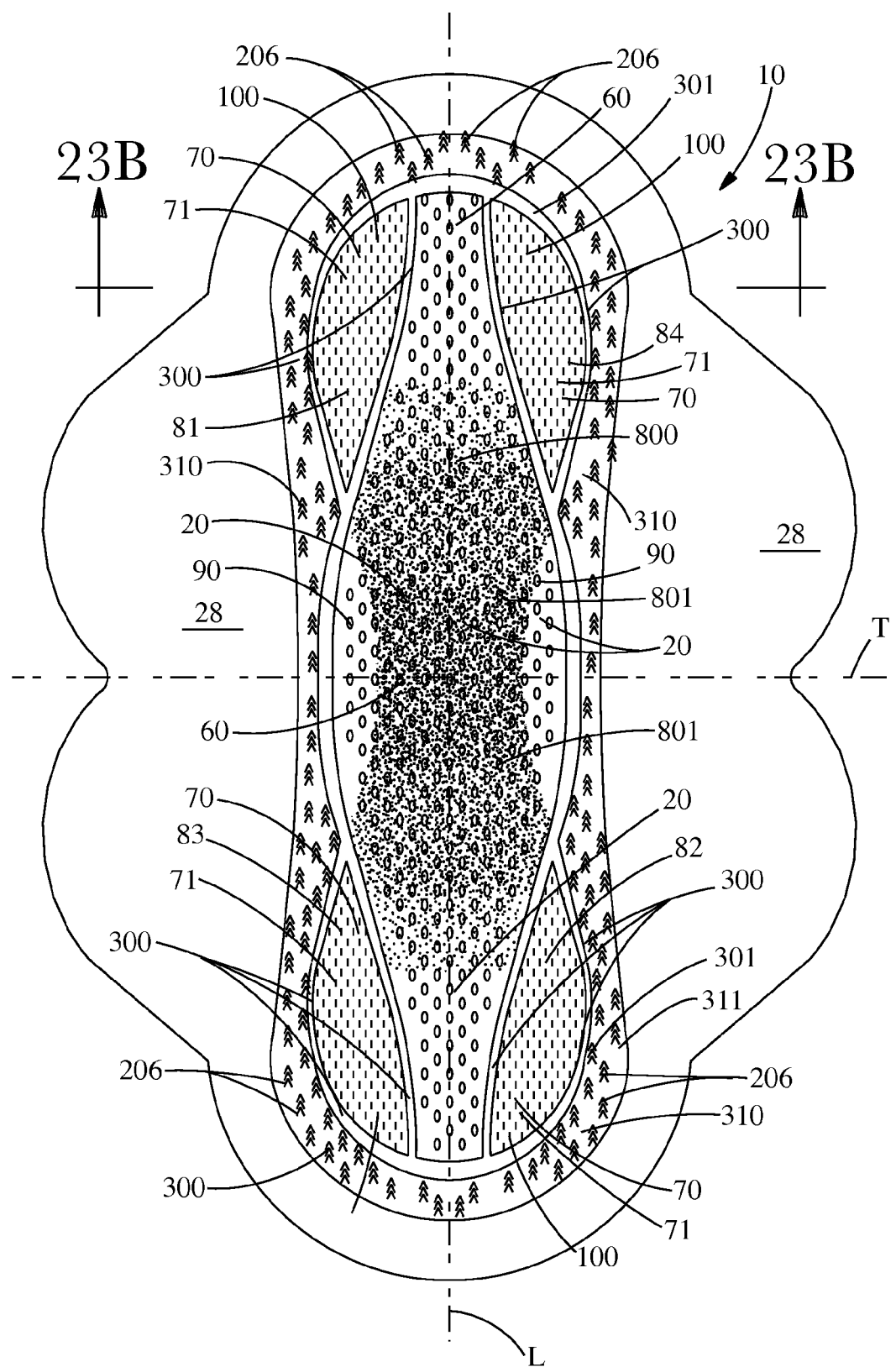
FIG. 23A is an illustration of an absorbent article having colored channels and a printed zone.

In one embodiment, as shown in FIG. 23A the structurally modified zones can have a boundary wherein at least part of the boundary is defined by a channel 300. That is, for one or more of the structurally modified zones, a channel 300 can surround or partially surround the structurally modified zone and can be contiguous with that particular structurally modified zone. Channel 300 can be formed by any means known in the art for creating channels in absorbent articles. Suitable processes include compression molding in which the topsheet 20 and absorbent core 40 are compressed leaving an indentation in the body facing surface of the absorbent article. Without being bound by theory, it is thought that the capillary potential of the portion of the absorbent core 40 near a channel 300 can be higher than the capillary potential of portions of the absorbent core 40 away from the channel 300 and that the higher capillary potential can resist fluid transport beyond the channel 300. Similarly, the first portion 60 can also have a boundary wherein at least part of the boundary is defined by a channel 300.

In one embodiment, the topsheet 20 can comprise a third portion 310, as shown in FIG. 23A. The third portion 310 can at least partially bound or even completely bound both the first portion 60 and the second portion 70 in the plane defined by the longitudinal centerline and transverse centerline of the topsheet 20. The third portion 310 can be an apertured web having structures as disclosed above for the first portion 60 and second portion 70. The third portion 310 can comprise tufts 206, as shown in FIG. 23A. The third portion 310 can differ in structure from the first portion 60. The third portion 310 can differ in structure from the second portion 70. The third portion 310 can differ in structure from the first portion 60 and the second portion 70. The third portion 310 can differ in structure from a portions or portions selected from the group consisting of the first portion, the second portion, and both the first portion and second portion. Without being bound by theory, it is thought that by arranging a third portion 310 in this manner, the topsheet 20 can be provided with a peripheral structure that can be comforting to the wearer's skin and/or provide a barrier for flow of fluid on or near the surface of the absorbent article 10. In the context of a sanitary napkin worn in the crotch region, the third portion 310 at the front and back of the sanitary napkin can reduce the potential for leakage off of the sanitary napkin in these areas when the woman is lying on her back or front. The third portion 310 along the sides of the sanitary napkin can reduce the potential for lateral runoff from the sanitary napkin. The third portion 310 can comprise structures other than tufts 206.

In one embodiment, the third portion 310 can comprise tufts 206 of a soft nonwoven web. A third portion 310 comprising tufts 206 can provide for improved comfort of the absorbent article 10 when worn given that the peripheral edges of the absorbent article 10 may rub against the wearer's skin in her crotch area. The first portion 60 and/or second portion 70 of the topsheet 20 can be an apertured film having sufficient fluid acquisition characteristics and the third portion 310 can comprise tufts 206 formed of a nonwoven material to provide for comfort. This approach can provide for an absorbent article 10 that has adequate fluid acquisition properties near the center of the absorbent article 10 and can provide for comfort about the periphery of the absorbent article 10.

Figure 23B:
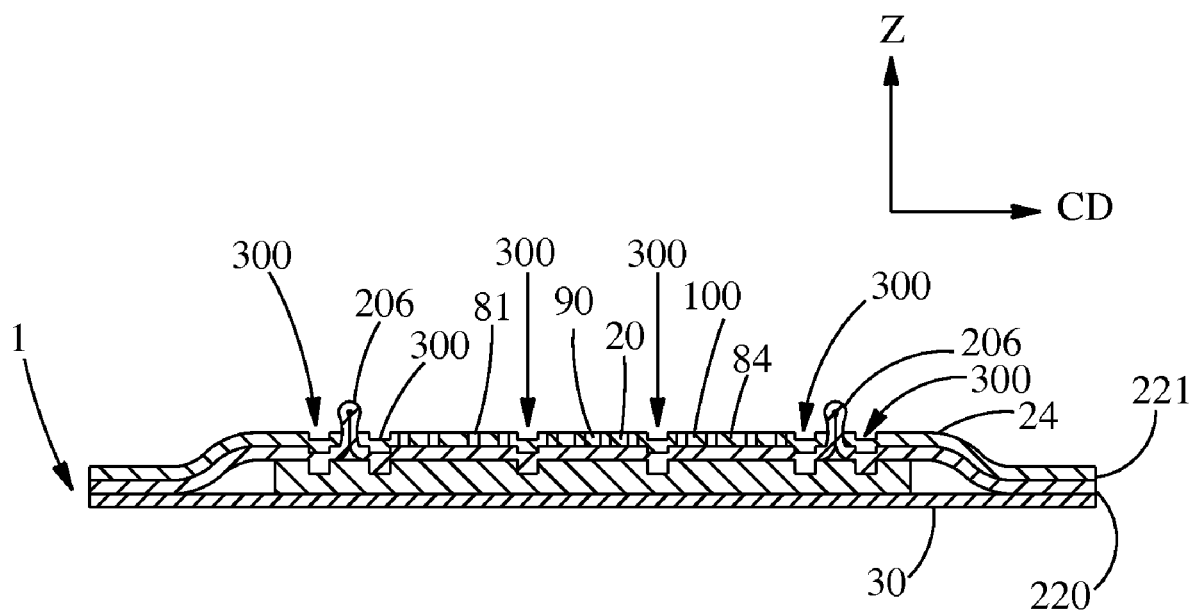
FIG. 23B a cross section as indicated by Section 23B in FIG. 23A.

A channel 300 can have at least a portion in which the color differs from the color of the second portion 70. As shown in FIG. 23A, the second portion 70 can have a second color 71. That is, the channel color 301 of at least a portion of a channel 300 can differ from the color of at least a portion of one or more of the structurally modified zones (for example first structurally modified zone 81, second structurally modified zone 82, third structurally modified zone 83, and fourth structurally modified zone 84). A cross section as marked in FIG. 23A is illustrated in FIG. 23B. The channel color 301 and/or second color 71 can be printed or appear on the topsheet 20 or can be printed or appear on a layer underlying the topsheet 20 such that a color is visible through the topsheet 20 when the absorbent article 10 is viewed from the body facing side of the absorbent article 10. The colored portion of channel 300, if present, can have a color that varies along the channel 300. Color can be printed on the topsheet 20 and/or underlying layer or layers by processes known in the art including, but not limited to, ink jet printing gravure printing, offset printing, and combinations thereof. The constituent material or materials of the colored portions of the topsheet 20 or underlying layers can be colored. The first portion 60 can also have a boundary wherein at least part of the boundary is defined by a channel 300 and at least part of the channel has a channel color 301 that differs from the color of the first portion 60. Colored channels 300 may effectively communicate and highlight that the structurally modified zones may be zones having enhanced performance and can provide confidence to the wearer that she is wearing a high performance absorbent article 10 and provide visual contrast between boundaries of the absorbent article 10 and the fluids absorbed.

The absorbent article 10 can further comprise a printed zone 800 along at least a portion of the longitudinal centerline, the printed zone 800 having a printed zone color 801. The printed zone color 801 can vary along the longitudinal centerline, as shown in FIG. 23A. The printed zone 800 can be on the topsheet 20 or on a layer underlying the topsheet 20 such that the color is visible through the topsheet 20 when the absorbent article 10 is viewed from the body facing surface side of the absorbent article 10. Color can be printed on the topsheet 20 and/or underlying layer or layers by processes known in the art including, but not limited to, ink jet printing, gravure printing, offset printing, and combinations thereof. The constituent material or materials of the colored portions of the topsheet 20 or underlying layers can be colored. Without being bound by theory, it is thought that the printed zone 800 can assist the wearer in placing the pad in the appropriate location of her panty, support observation of fluid spreading to learn about proper wear time, and also can indicate to the wearer where absorbency may be greatest.

Figure 24:
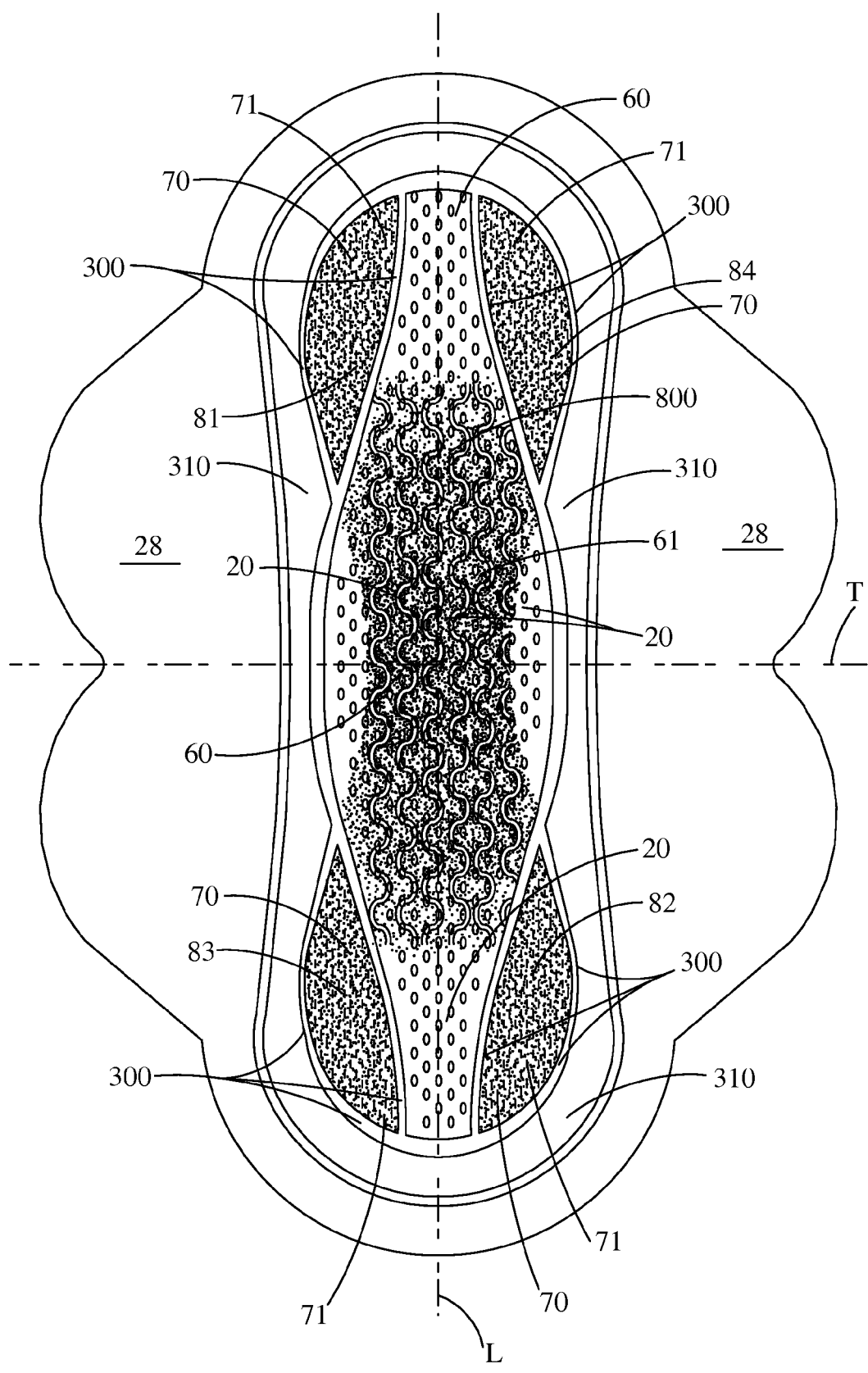
FIG. 24 is an illustration of an absorbent article having a first portion having a first color and a second portion having a second color.

As illustrated in FIG. 24, the first portion 60 can have a first color 61 and the second portion 70 can have a second color 71, wherein the first color 61 differs from the second color 71. The third portion 310, if present, can have a third color 311 wherein the third color 311 of the third portion 310 differs from a color selected from the group consisting of the first color 61, the second color 71, and both the first color 61 and the second color 71. Without being bound by theory, it is thought that the difference in colors can aid the wearer in properly placing the absorbent article 10 in her panty. The wearer can correlate the relative location of different portions of the absorbent article 10, which can be identified by color, with the staining pattern (from bodily discharge) and make judgments about proper placement and wear time. The difference in colors can also communicate the difference in performance of different portions of the absorbent article 10 and provide the wearer with visual cues, such as contrasting colors, regarding wear time, fluid entry, and fluid spreading.

The difference in color can be greater than about 3.5, as characterized by the CIE LAB scale. The difference in color can be greater than about 1.1, as characterized by the CIE LAB scale. The difference in color can be greater than about 6, as characterized by the CIE LAB scale.

Absorbent core 40 can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

In one embodiment absorbent core 40 can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa. The absorbent core can comprise absorbent gelling materials (AGM), including AGM fibers, as is known in the art.

Backsheet 30 can comprise any of the materials known in the art for backsheets, such as polymer films and film/nonwoven laminates. To provide a degree of softness and vapor permeability for the garment-facing side of absorbent article 10, backsheet 30 can be a vapor permeable outer layer on the garment-facing side of the absorbent article 10. The backsheet 30 can be formed from any vapor permeable material known in the art. Backsheet 30 can comprise a microporous film, an apertured formed film, or other polymer film that is vapor permeable, or rendered to be vapor permeable, as is known in the art. One suitable material is a soft, smooth, compliant, vapor pervious material, such as a nonwoven web that is hydrophobic or rendered hydrophobic to be substantially liquid impermeable.

Other materials and components of absorbent articles 10 are contemplated to be within the scope of the description, including those disclosed in U.S. Pat. No. 4,950,264 issued to Osborn III Aug. 21, 1990 and U.S. Pat. No. 5,439,458 issued to Noel et al. Aug. 8, 1995.

Components of the absorbent article 10 can be joined by any means known in the art, such as by adhesive bonding, thermal bonding, ultrasonic bonding, and the like. An adhesive can be applied by means known in the art for laying a uniform layer of adhesive, such as by spraying or slot coating. The adhesive can be a fluid permeable adhesive, such as the aforementioned Findley HX1500-1 adhesive.

EXAMPLE

FIG. 23A and FIG. 23B illustrate an example of a topsheet 20 that has a first portion 60 and a second portion 70. The second portion 70 of the topsheet 20 can comprise a first structurally modified zone 81, a second structurally modified zone 82, a third structurally modified zone 83, and a fourth structurally modified zone 84. The first apertures 90 can be formed by a portion of roll 104, shown in FIG. 7, that is 100 pitch. Second apertures 100 in the second portion 70 can be formed by a portion of roll 104, shown in FIG. 7, that is 50 pitch. The first structurally modified zone 81, a second structurally modified zone 82, a third structurally modified zone 83, and a fourth structurally modified zone can be bound by a channel 300 that has a width ranging from about 1.5 mm to about 4.2 mm A third portion 310 bounds both the first portion 60 and the second portion 70. The third portion 310 can comprise tufts 206 of a nonwoven first precursor web 220 protruding through a film second precursor web 221.

A differences in color can be characterized using the CIE LAB scale and measured using a Hunter Labscan XE 45/0 geometry reflectance spectrophotometer. Technical description of the system can be found in an article by R. S. Hunter, 'photoelectric color difference Meter', Journal of the Optical Society of America, Vol. 48, pp. 985-95, 1958. Devices that are specially designed for the measurement of color on the Hunter scales are described in U.S. Pat. No. 3,003,388 to Hunter et al., issued Oct. 10, 1961.

Colors can be measured according to an internationally recognized 3D solid diagram of colors where all colors that are perceived by the human eye are converted into a numerical code. The CIE LAB system is similar to Hunter L, a, and b and is based on three dimensions, specifically L*, a*, and b*.

When a color is defined according to this system L* represents lightness (0=black, 100=white), a* and b* independently each represent a two color axis, a* representing the axis red/green (+a=red, −a=green), while b* represents the axis yellow/blue (+b=yellow, −b=blue).

A color may be identified by a unique ΔE value (i.e., different in color from some standard or reference), which is mathematically expressed by the equation:

$$\Delta E^* = [(L^*X. - L^*Y)^2 + (a^*X. - a^*Y)^2 + (b^*X - b^*Y)^2]^{1/2}$$

'X' represents the standard or reference sample and 'Y' is the variant.

The Hunter color meter is configured to yield 3 values (L*, a*, b* and ΔE* which is total color). The L* value is the percent of the incident (source) light that is reflected off a target sample and onto the detector. A shiny white sample will yield an L* value near 100. A dull black sample will yield an L* value of about 0. The a* and b* value contains spectral information for the sample. Positive a* value indicates the amount of green in the sample.

The diameter of the port is to be selected based on the area upon which color measurement is to be made, with the size of the port being the largest port available that provides for an area view that is smaller than the area upon which color measurement is made. A 0.2 inch diameter port can be used. A 0.7 inch diameter port can be used having a 0.5 inch area view. The instrument is to be calibrated using standard white and black tiles supplied by the instrument manufacturer prior to use for measurements.

A standard, industry-recognized procedure is used to measure the L*, a*, and b* values. The color of parts of the topsheet is measured using a reflectance spectrophotometer in accordance with method ASTM E 1164-94, "Standard Practice for Obtaining Spectrophotometric Data for Object-Color Evaluation". This standard method is followed but specific instrument settings and sampling procedure are given here for clarity. Sample color can be reported in terms of the CIE 1976 color coordinate standard as specified in ASTM E 1164-94 and ASTM D2264-93, section 6.2. This consists of three values; L* which measures sample "lightness", a* which measures redness or greenness, and b* which measures yellowness or blueness.

Apparatus

Reflectance Spectrophotometer . . . 45°/0° Hunter Labscan XE, or equivalent

HunterLab Headquarters, 11491 Sunset Hills Road, Reston Va. 20190-5280 Tel: 703-471-6870 Fax: 703-471-4237, http://www.hunterlab.com.

Standard plate . . . Standard Hunter White Tile Source: Hunter Color.

Equipment Preparation

1. Assure that the Spectrophotometer is configured as follows:

Illumination . . . Type C
Standard Observer . . . 2°
Geometry . . . 45/0° Measurement angle
Port Diameter . . . select port diameter based upon the area upon which color measurement is to be made
Viewing area . . . to be selected based upon the area upon which color measurement is to be made
UV Filter: Nominal 2. Calibrate the spectrophotometer using standard black and white tiles supplied with the instrument according to manufacturer's instructions before beginning any testing.

Sample Preparation

1. Unwrap, unfolded and lay the product or article samples flat without touching or altering the color of the body facing surface.

2. Areas on the viewing surface of the product should be selected for measurement and must include the following:

The reference region of the viewing surface.
The variant region of the viewing surface.
Any other portions of the viewing surface having a visibly or measurably different color from the reference or variant region. Measurements should not be made overlapping the border of two shaded portions.

Test Procedure

1. Operate the Hunter Colorimeter according to the instrument manufacturer's instructions.

2. The absorbent article should be measured laying flat over the aperture on the instrument. A white tile should be placed behind the pad.

3. The absorbent article should be placed with its long direction perpendicular to the instrument.

4. Measure the same zones selected above for at least 3 replicate samples.

Calculation Reporting

1. Ensure that the reported results are really CIE L*,a*,b*.
2. Record the L*,a*,b* values to the nearest 0.1 units.
3. Take the average L*, a*, b* for each zone measured.
4. Calculate ΔE* between a colored region and the background.

A portion can be considered to have a color that differs from a reference color if ΔE is greater than or equal to about 3.5. A portion can be considered to have a color that differs from a reference color if ΔE is greater than or equal to about 1.0.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a liquid pervious topsheet comprising a first portion and a second portion, wherein said first portion differs in structure from said second portion, said topsheet having an area;

wherein said topsheet has a longitudinal centerline and a transverse centerline;

wherein said second portion comprises a first structurally modified zone, a second structurally modified zone, a third structurally modified zone, and a fourth structurally modified zone;

wherein said first structurally modified zone and said second structurally modified zone are on opposing sides of said longitudinal centerline and said first structurally modified zone and said second structurally modified zone are on opposing sides of an axis parallel to said transverse centerline;

wherein said third structurally modified zone is disposed on the same side of said longitudinal centerline as said first structurally modified zone, wherein said first structurally modified zone and said third structurally modified zone are disposed on opposing sides of an axis parallel to said transverse centerline;

wherein said fourth structurally modified zone is disposed on the same side of said longitudinal centerline as said second structurally modified zone, wherein said second structurally modified zone and said fourth structurally modified zone are disposed on opposing sides of an axis parallel to said transverse centerline;

wherein said first structurally modified zone, said second structurally modified zone, said third structurally modified zone, and said fourth structurally modified zone are spaced apart from one another;

wherein said first structurally modified zone, said second structurally modified zone, said third structurally modified zone, and said fourth structurally modified zone together comprise more than about 10% of the area of said topsheet;

wherein said first structurally modified zone is different from said third structurally modified zone through a difference in size or pattern of structures defining the respective first and third structurally modified zones, and wherein said second structurally modified zone is different from said fourth structurally modified zone through a difference in size or pattern of structures defining the respective second and fourth structurally modified zones.

2. The absorbent article according to claim 1, wherein said first structurally modified zone, said second structurally modified zone, said third structurally modified zone, and said fourth structurally modified zone are defined by a plurality of spaced apart macro features having a maximum spacing, wherein said first structurally modified zone, said second structurally modified zone, said third structurally modified zone, and said fourth structurally modified zone are spaced apart from one another by a distance greater than said maximum spacing between adjacent macro features.

3. The absorbent article according to claim 1, wherein said first structurally modified zone, said second structurally modified zone, said third structurally modified zone, and said fourth structurally modified zone are defined by a plurality of spaced apart micro features having a maximum spacing, wherein said first structurally modified zone, said second structurally modified zone, said third structurally modified zone, and said fourth structurally modified zone are spaced apart from one another by a distance greater than said maximum spacing between adjacent micro features.

4. The absorbent article according to claim 1, wherein said first portion comprises first apertures and said second portion comprises second apertures, wherein said first apertures differ in structure from said second apertures.

5. The absorbent article according to claim 4, wherein said first apertures have a first size and said second apertures have a second size, wherein said second size of said second apertures is greater than said first size of said first apertures.

6. The absorbent article according to claim 1, wherein said first portion comprises first apertures and said second portion comprises second apertures, wherein said first portion has a first portion aperture area density and said second portion has a second portion aperture area density, wherein said first portion aperture area density differs from said second portion aperture area density.

7. The absorbent article according to claim 1, wherein said longitudinal centerline and said transverse centerline of said topsheet define an in-plane orientation of said topsheet, wherein said first portion has a first portion out-of-plane geometry and said second portion has a second portion out-of-plane geometry, wherein said first portion out-of-plane geometry differs from said second portion out-of-plane geometry.

8. The absorbent article according to claim 7, wherein said first portion comprises first apertures and said second portion comprises second apertures, wherein said first apertures differ in structure from said second apertures.

9. The absorbent article according to claim 8, wherein said first apertures have a first size and said second apertures have a second size, wherein said second size of said second apertures is greater than said first size of said first apertures.

10. The absorbent article according to claim 7, wherein said first portion comprises a laminate web comprising a first precursor web and second precursor web, at least said first precursor web being a nonwoven web, said laminate web having a first side, said first side comprising the second precursor web and at least one discrete tuft, each of said discrete tufts comprising a plurality of tufted fibers being integral extensions of the first precursor web and extending through the second precursor web, said laminate web having a second side, said second side comprising the first precursor web.

11. The absorbent article according to claim 7, wherein said second portion comprises a laminate web comprising a first precursor web and second precursor web, at least said first precursor web being a nonwoven web, said laminate web having a first side, said first side comprising the second precursor web and at least one discrete tuft, each of said discrete tufts comprising a plurality of tufted fibers being integral extensions of the first precursor web and extending through the second precursor web, said laminate web having a second side, said second side comprising the first precursor web.

12. The absorbent article according to claim 1, wherein at least part of a boundary of a structurally modified zone selected from the group consisting of said first structurally modified zone, said second structurally modified zone, said third structurally modified zone, and said fourth structurally modified zone is defined by a channel.

13. The absorbent article according to claim 12, wherein said channel has a channel color and said second portion has a second color, wherein said channel color of at least a portion of said channel differs from said second color.

14. The absorbent article according to claim 1, wherein said first portion has a first color and said second portion has a second color, wherein said first color differs from said second color.

15. The absorbent article according to claim 1 further comprising a printed zone along at least a portion of said longitudinal centerline, wherein said printed zone has a printed zone color, wherein said printed zone color varies along said longitudinal centerline.

16. The absorbent article according to claim 1, wherein said topsheet comprises a third portion, wherein said third portion at least partially bounds said first portion and said second portion in a plane defined by said longitudinal centerline and said transverse centerline of said topsheet, wherein said third portion differs in structure from a portion or portions selected from the group consisting of said first portion, said second portion, and both said first portion and said second portion.

17. The absorbent article according to claim 16, wherein said third portion comprises a laminate web comprising a first precursor web and second precursor web, at least said first precursor web being a nonwoven web, said laminate web having a first side, said first side comprising the second precursor web and at least one discrete tuft, each of said discrete tufts comprising a plurality of tufted fibers being integral extensions of said first precursor web and extending through said second precursor web, said laminate web having a second side, said second side comprising said first precursor web.

18. The absorbent article according to claim 16, wherein said first portion has a first color, said second portion has a second color, and said third portion has a third color, wherein said third color differs from a color selected from the group consisting of said first color, said second color, and both said first color and said second color.

19. The absorbent article according to claim 1, further comprising a backsheet and an absorbent core disposed between said topsheet and said backsheet, wherein said absorbent article is a consumer product selected from the group consisting of a sanitary napkin, an adult incontinence product, and a diaper.

20. The absorbent article according to claim 1, wherein said absorbent article has a length and a width, wherein said first structurally modified zone, said second structurally modified zone, said third structurally modified zone, and said fourth structurally modified zone each have an area that is more than about 5% of the length of the absorbent article and 5% of the width of the absorbent article, the width being measured at the centroid of the respective zone.

* * * * *